(12) United States Patent
Parlanti et al.

(10) Patent No.: US 8,143,415 B2
(45) Date of Patent: Mar. 27, 2012

(54) PROCESSES FOR MAKING EPOTHILONE COMPOUNDS AND ANALOGS

(75) Inventors: Luca Parlanti, New York, NY (US); Jurong Yu, Dayton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 149 days.

(21) Appl. No.: 12/601,834

(22) PCT Filed: May 23, 2008

(86) PCT No.: PCT/US2008/064627
§ 371 (c)(1),
(2), (4) Date: Nov. 25, 2009

(87) PCT Pub. No.: WO2008/147941
PCT Pub. Date: Dec. 4, 2008

(65) Prior Publication Data
US 2010/0324302 A1    Dec. 23, 2010

Related U.S. Application Data

(60) Provisional application No. 60/940,088, filed on May 25, 2007.

(51) Int. Cl.
C07D 417/00    (2006.01)
C07D 277/20    (2006.01)
C07D 277/30    (2006.01)

(52) U.S. Cl. .......... 548/181; 548/202; 548/204

(58) Field of Classification Search .......... 548/202, 548/204, 181
See application file for complete search history.

(56) References Cited

U.S. PATENT DOCUMENTS

| | | | |
|---|---|---|---|
| 5,416,016 A | 5/1995 | Low et al. | |
| 6,156,905 A * | 12/2000 | Schinzer et al. | 548/204 |
| 6,262,094 B1 | 7/2001 | Hoefle et al. | |
| 6,291,673 B1 | 9/2001 | Fuchs et al. | |
| 6,291,684 B1 | 9/2001 | Borzilleri et al. | |
| 6,380,395 B1 | 4/2002 | Vite et al. | |
| 6,399,638 B1 | 6/2002 | Vite et al. | |
| 6,498,257 B1 | 12/2002 | Vite et al. | |
| 6,605,599 B1 | 8/2003 | Vite et al. | |
| 6,624,310 B1 | 9/2003 | Hoefle et al. | |
| 6,800,653 B2 | 10/2004 | Regueiro-Ren et al. | |
| 7,601,332 B2 | 10/2009 | Vlahov et al. | |
| 7,872,145 B2 * | 1/2011 | Vite et al. | 548/202 |
| 2004/0127432 A1 | 7/2004 | Nicolaou et al. | |
| 2007/0275904 A1* | 11/2007 | Vite et al. | 514/18 |
| 2007/0276018 A1* | 11/2007 | Vite et al. | 514/365 |

FOREIGN PATENT DOCUMENTS

| | | |
|---|---|---|
| WO | WO 93/10121 | 5/1993 |
| WO | WO 00/66091 | 11/2000 |
| WO | WO 02/098868 | 12/2002 |
| WO | WO 03/045324 | 6/2003 |
| WO | WO 2004/012735 | 2/2004 |
| WO | WO 2004/054622 | 7/2004 |
| WO | WO 2005/074901 | 8/2005 |
| WO | WO 2006/042146 | 4/2006 |
| WO | WO 2007/140297 | 12/2007 |
| WO | WO 2007/140298 | 12/2007 |

OTHER PUBLICATIONS

Katritzky et al. Comprehensive Organic Functional Group Transformations, vol. 2, First Edt. 1995; p. 17 and 18.*
Antony, A.C., "Folate receptors: reflections on a personal odyssey and a perspective on unfolding truth", Advanced Drug Delivery Reviews, vol. 56, pp. 1059-1066 (2004).
Elnakat, H. et al., "Distribution, functionality and gene regulation of folate receptor isoforms: implications in targeted therapy", Advanced Drug Delivery Reviews, vol. 56, pp. 1067-1084 (2004).
Gabizon, A. et al., "Tumor cell targeting of liposome-entrapped drugs with phospholipid-anchored folic acid—PEG conjugates", Advanced Drug Delivery Reviews, vol. 56, pp. 1177-1192 (2004).
Jackman, A.L. at al., "Antifolates targeted specifically to the folate receptor", Advanced Drug Delivery Reviews, vol. 56, pp. 1111-1125 (2004).
Kamen, B.A. et al., "A review of folate receptor alpha cycling and 5-methyltetrahydrofolate accumulation with an emphasis on cell models in vitro", Advanced Drug Delivery Reviews, vol. 56, pp. 1085-1097 (2004).

(Continued)

Primary Examiner — Andrew D Kosar
Assistant Examiner — Valerie Rodriguez-Garcia
(74) Attorney, Agent, or Firm — Yuan Chao; Laurelee L. Duncan

(57) ABSTRACT

A process for making epi-epothilone compounds according to formula A.1,

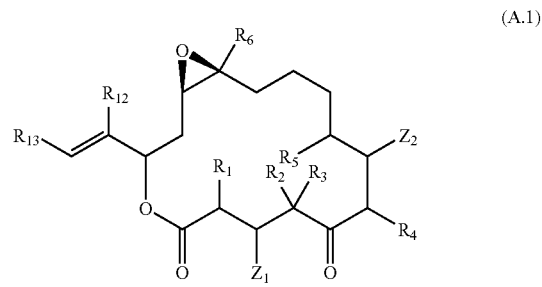

by reacting a compound according formula C

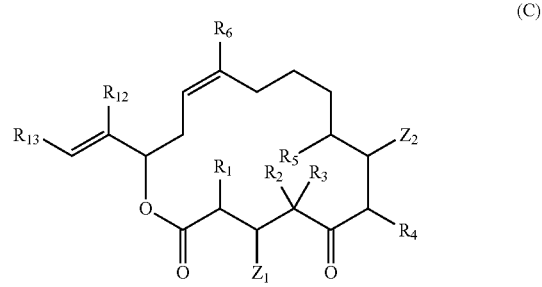

with at least one halogenating agent followed by treatment with base, where $R_1$, $R_2$, $R_3$, $R_4$, $R_5$, $R_6$, $R_{12}$, $R_{13}$, $Z_1$ and $Z_2$ in formulae (A.1) and (C) are as defined herein. The epi-epothilone compounds of formula (A.1) can be converted into aziridinyl epothilone compounds, which are useful for the treatment of cancer.

15 Claims, No Drawings

OTHER PUBLICATIONS

Ke, C.-Y. et al., "Folate-receptor-targeted radionuclide imaging agents", Advanced Drug Delivery Reviews, vol. 56, pp. 1143-1160 (2004).

Leamon, C.P. et al., "Folate-targeted chemotherapy", Advanced Drug Delivery Reviews, vol. 56, pp. 1127-1141 (2004).

Low, P.S. et al., "Folate-receptor-targeted drugs for cancer and inflammatory diseases", Advanced Drug Delivery Reviews, vol. 56, pp. 1055-1058 (2004).

Lu, Y. et al., "Folate receptor-targeted immunotherapy of cancer: mechanism and therapeutic potential", Advanced Drug Delivery Reviews, vol. 56, pp. 1161-1176 (2004).

Melby, E.L. et al., "Entry of Protein Toxins in Polarized Epithelial Cells", Cancer Research, vol. 53, pp. 1755-1760 (1993).

Olsnes, S. et al., "Immunotoxins—entry into cells and mechanisms of action", Immunology Today, vol. 10, No. 9, pp. 291-295 (1989).

Paulos, C.M. et al., "Folate receptor-mediated targeting of therapeutic and imaging agents to activated macrophages in rheumatoid arthritis", Advanced Drug Delivery Reviews, vol. 56, pp. 1205-1217 (2004).

Regueiro-Ren, A. et al., "Synthesis and Biological Activity of Novel Epothilone Aziridines", Organic Letters, vol. 3, No. 17, pp. 2693-2696 (2001).

Roy, E.J. et al., "Folate-mediated targeting of T cells to tumors", Advanced Drug Delivery Reviews, vol. 56, pp. 1219-1231 (2004).

Sabharanjak, S. et al., "Folate receptor endocytosis and trafficking", Advanced Drug Delivery Reviews, vol. 56, pp. 1099-1109 (2004).

Zhao, X.B. et al., "Tumor-selective targeted delivery of genes and antisense oligodeoxyribonucleotides via the folate receptor", Advanced Drug Delivery Reviews, vol. 56, pp. 1193-1204 (2004).

* cited by examiner

PROCESSES FOR MAKING EPOTHILONE COMPOUNDS AND ANALOGS

FIELD OF THE INVENTION

The present invention relates to processes for making epothilone compounds and analogs thereof, such as epi-epothilone A or epi-epothilone B, and aziridinyl-epothilone analogs.

BACKGROUND OF THE INVENTION

Epothilones A and B are naturally-occurring compounds that were discovered by Höfle et al. as isolated from fermentation products of the microorganism, *Sorangium cellulosum* (see, e.g., WO 93/10121). Höfle et al. also discovered 37 natural epothilone variants and related compounds produced by *Sorangium cellulosum*, including epothilones C, D, E, F and other isomers and variants. See, e.g., U.S. Pat. No. 6,624,310.

Epothilones A and B are major metabolites of *Sorangium cellulosum* and as natural products, have the following stereospecific forms:

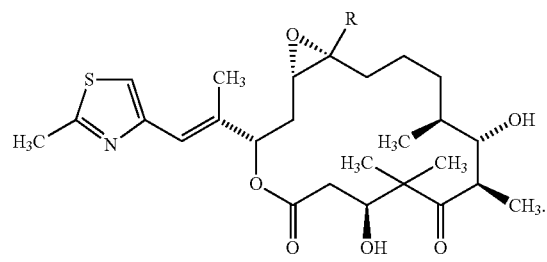

R = H, epothilone A
R = CH₃, epothilone B

Various derivatives and analogs of the naturally-occurring epothilones have been discovered at Bristol-Myers Squibb Company. Examples of such epothilone analogs include the aza-epothilone B analog known as ixabepilone and aziridinyl-epothilone analogs. See, e.g., U.S. Pat. Nos. 6,605,599; 6,262,094; 6,399,638; 6,498,257; 6,380,395; and 6,800,653.

Certain aziridinyl-epothilone have been discovered as especially useful in preparing compositions for targeted drug therapies in treating cancer, as disclosed in U.S. provisional application Ser. No. 60/808,366, filed May 25, 2006, and U.S. patent application Ser. No. 11/735,785, titled "Azirdinyl-Epothilone Compounds," (US2007/0276018A1, published 29 Nov. 2007) claiming priority to the 60/808,366 application, assigned to the present assignee, which is hereby incorporated by reference.

Processes for making aziridinyl-epothilone analogs from oxiranyl epothilones are disclosed in U.S. Pat. No. 6,291,684 to Borzilleri et al., and assigned to the present assignee. In Borzilleri, aziridinyl-epothilones are prepared from compounds having stereoconfigurations aligned with epothilones A or B. With these stereospecific compounds, several steps are then taken to make the aziridinyl-epothilones, including breaking the epoxide ring upon reaction with a metal halide, converting the halide to an azide upon reaction with an azide salt, conducting a Mitsunobu reaction to form an intermediate ester, cleaving the ester to form an intermediate azidoalcohol, and then cyclizing the azidoalcohol to provide the aziridinyl-epothilone compounds. See, e.g., U.S. Pat. No. 6,291,684 B1, cols. 2-3. Reportedly, this multi-step process is used to obtain aziridinyl-epothilone compounds retaining the stereoconfiguration of the starting materials. (Col. 1, l. 57-60).

In Regueiro-Ren et al., *Organic Letters*, 3:2693-2696 (2001), there is disclosed a scheme for making aziridinyl-epothilones via an intermediate diastereomeric epothilone A, or epi-epothilone A ("epi-epo A"). Regueiro-Ren et al. report the following Scheme:

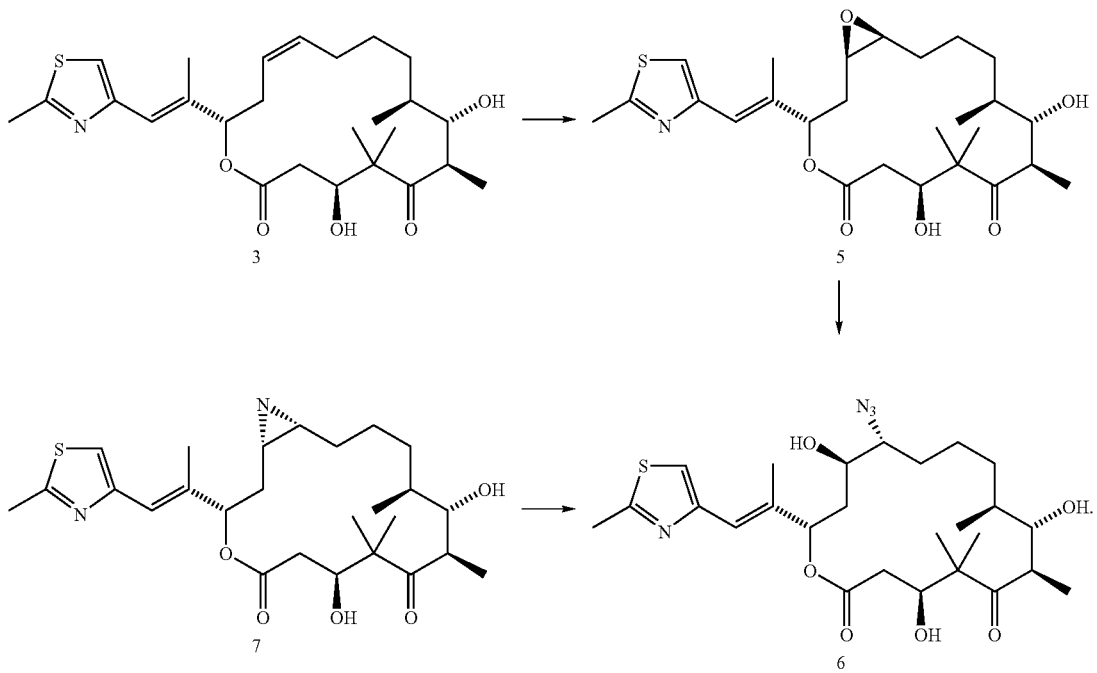

Regueiro-Ren et al state that epoxidation of 3 gave the desired 12β,13β-epoxide 5 (epi-epo A) but in a ratio of epothilone A to 12β,13β-epothilone A of 3:1. Regueiro-Ren et al. further report that attempts to alter and improve this ratio in favor of the desired 12β,13β-epoxide 5 were unsuccessful, and that other reaction conditions including low temperature, solvent variation, and alternative dioxirane source had no effect on the diastereoselectivity. Regueiro-Ren et al. at page 2694, footnote 8.

Accordingly, there is presented the technical problem of developing efficient processes for making epothilones and analogs, for example, for making epi-epothilones such as epi-epo A or epi-epo B with improved ratios of the epi-stereospecific forms, and for making epothilone analogs such as azirdinyl-epothilone analogs using the epi-epothilones as intermediates.

SUMMARY OF THE INVENTION

The present invention provides improved processes for making epi-epothilones, such as epi-epo A/B and protected forms of epi-epo A/B, useful as an intermediates, providing significantly improved ratios of the epi-stereospecific forms (e.g., as compared with the major, naturally-configured isomers) and to improved processes for converting the epi-epothilones into aziridinyl-epothilone compounds.

In one embodiment, the present invention provides a process comprising (i) reacting a compound having the formula (g,

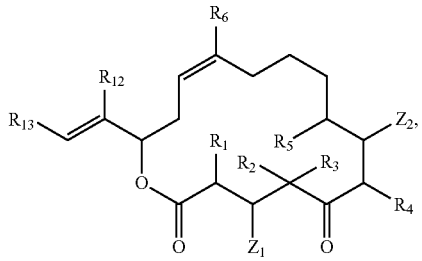

(C)

wherein, $R_1$ is hydrogen or forms a bond with $Z_1$;

$Z_1$ is hydroxyl, cyano, is taken together with $R_1$ to form a bond, or is $OR_p$;

$Z_2$ is hydroxyl or $OR_p$; wherein each $R_p$ is a protecting group;

$R_2$, $R_3$, and $R_5$ are independently, hydrogen, alkyl, substituted alkyl, aryl or substituted aryl; or $R_2$ and $R_3$ may be taken together with the carbon to which they are attached to form an optionally-substituted cycloalkyl;

$R_4$ is hydrogen, alkyl, substituted alkyl, alkenyl, alkynyl, aryl, or substituted aryl;

$R_6$ is hydrogen, alkyl or substituted alkyl;

$R_{12}$ is hydrogen, alkyl, substituted alkyl, or halogen; and $R_{13}$ is aryl, substituted aryl, heteroaryl or substituted heteroaryl;

(ii) with a halogenating agent to provide compounds having the formulae (B.1) and (B.2),

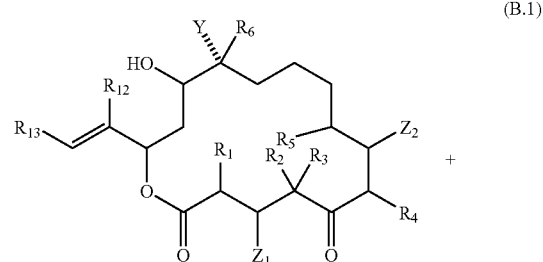

(B.1)

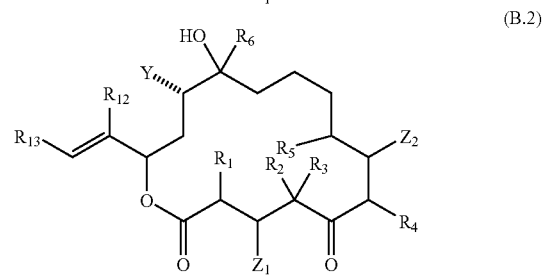

(B.2)

wherein Y is halogen, and $R_1$, $R_2$, $R_3$, $R_4$, $R_5$, $R_6$, $R_{12}$, $R_{13}$, $Z_1$ and $Z_2$ are as previously described; and (iii) performing an epoxide ring closure of compounds of formula (B.1) and/or (B.2) to provide a compound of formula (A.1),

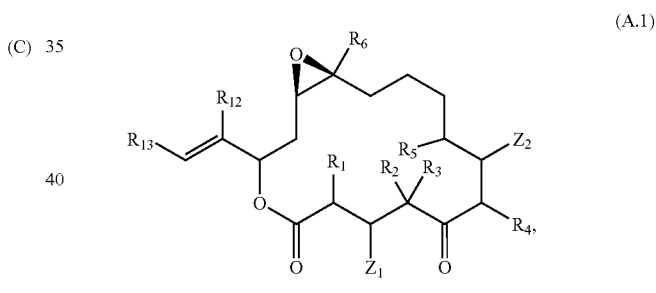

(A.1)

wherein $R_1$, $R_2$, $R_3$, $R_4$, $R_5$, $R_6$, $R_{12}$, $R_{13}$, $Z_1$ and $Z_2$ are as previously described.

Compounds of formula (A.1) are particularly useful in making aziridinyl-epothilone compounds having microtubule-stabilizing effects, such as those having the formula (H), as described below.

In another embodiment, processes are provided for making aziridinyl-epothilones analogs, such as those having the formulae G or H, below, by treating compounds having the formula A.1, optionally prepared as summarized above, with an alkyl halide in the presence of base.

The above Summary of Invention is non-limiting, and further embodiments of the invention are described below.

DETAILED DESCRIPTION OF THE INVENTION
DEFINITIONS OF TERMS

The following are definitions of terms used in the present specification. The initial definition provided for a group or term herein applies to that group or term throughout the present specification individually or as part of another group, unless otherwise indicated.

Azide donor agents are nucleophiles capable of donating azide groups and may include inorganic azide salts, for example lithium or sodium azide, or tetra-alkyl ammonium azides, for example, tetrabutylammonium azide, trialkylsilyl azides, for example trimethylsilyl azide, and the like. Preferred azide donors are sodium azide and tetrabutyl ammonium azide.

"Base" when used herein includes metal oxides, hydroxides or alkoxides, hydrides, or compounds such as ammonia, that accept protons in water or solvent. Thus, exemplary bases include, but are not limited to, alkali metal hydroxides and alkoxides (i.e., MOR, wherein M is an alkali metal such as potassium, lithium, or sodium, and R is hydrogen or alkyl, as defined above, more preferably where R is straight or branched chain $C_{1-5}$ alkyl, thus including, without limitation, potassium hydroxide, potassium tert-butoxide, potassium tert-pentoxide, sodium hydroxide, sodium tert-butoxide, lithium hydroxide, etc.); other hydroxides such as magnesium hydroxide ($Mg(OH)_2$) or calcium hydroxide ($Ca(OH)_2$); alkali metal hydrides (i.e., MH, wherein M is as defined above, thus including, without limitation, sodium hydride and lithium hydride); alkylated disilazides, such as, for example, potassium hexamethyldisilazide and lithium hexamethyldisilazide; carbonates such as potassium carbonate ($K_2CO_3$), sodium carbonate ($Na_2CO_3$), potassium bicarbonate ($KHCO_3$), and sodium bicarbonate ($NaHCO_3$), alkyl ammonium hydroxides such as n-tetrabutyl ammonium hydroxide (TBAH); and so forth. Preferred bases herein include organic bases more particularly tertiary amines such as N-methylmorpholine, triethylamine, and diisopropylethylamine (a/k/a/ Hunig's base).

The term "coupling reagent" as used herein refers to a reagent used to couple a carboxylic acid and an amine or an aniline to form an amide bond. It may include a coupling additive, such as CDI, HOBt, HOAt, HODhbt, HOSu, or NEPIS, used in combination with another coupling reagent to speed up coupling process and inhibit side reactions. Particular peptide-coupling reagents may include DCC, EDC, BBC, BDMP, BOMI, HATU, HAPyU, HBTU, TAPipU, AOP, BDP, BOP, PyAOP, PyBOP, TDBTU, TNTU, TPTU, TSTU, BEMT, BOP—Cl, BroP, BTFFH, CIP, EDPBT, Dpp-Cl, EEDQ, FDPP, HOTT-PF6, TOTT-BF4, PyBrop, PyClop, and TFFH. See Peptide Coupling Reagents: Names, Acronyms and References, Albany Molecular Research, Inc., Technical Reports, Vol. 4, No. 1, incorporated herein by reference.

Elevated temperature herein means temperatures above room temperature (i.e., above about 25° C.), preferably at temperatures above about 30° C., and more preferably at temperatures of above about 30-40° C. One skilled in the field will recognize that the temperature selected for any particular reaction step may be limited by the choice of solvents or other reagents used in the particular step (e.g., by their boiling or melting points).

The terms "halogenating agent" or "halogenating reagent" mean an agent or agents capable of halogenating compounds of formula (C) (including C') herein. Halogenating reagents include inorganic and organic halogenating reagents. Examples of inorganic halogenating reagents include chlorine, bromine, iodine, fluorine, and sodium hypochlorite. Organic halogenating reagents include N-halosuccinimides such as N-chlorosuccinimide (NCS), N-bromosuccinimide (NBS), N-iodosuccinimide (NIS); or hydantions such as 1,3-dichloro-5,5-dimethylhydantoin, 1,3-dibromo-5,5-dimethylhydantoin, and 1,3-diiodo-5,5-dimethylhydantoin.

"High yield" as used herein means a yield of greater than 60%, more preferably greater than 70%, more preferably greater than 80%, even more preferably greater than 85%, and most preferably greater than 90%.

A "leaving group" means a group having the capability of being displaced upon reaction with a nucleophile including I, Br, Cl, $R_eSO_2O$— (wherein $R_e$ is alkyl, substituted alkyl, aryl, or heteroaryl, as defined herein), and weak bases, such as, for example, $HSO_4$—. Preferred leaving groups include ions of methyl sulfate, mesylate (methane sulfonate), trifluoromethanesulfonate, tosylate (p-toluenesulfonate), and nosylate.

"Protecting Group" as used herein means any protecting group known in the field, e.g., as defined Greene, T. W. et al., *Protective Groups in Organic Synthesis*, John Wiley and Sons, Inc. When a functional group is termed "protected", this means that the group is in modified form to mitigate, especially preclude, undesired side reactions at the protected site. Thus, a protecting group may be selected from alkyl, substituted alkyl (such as alkoxy alkyl, aryloxyalkyl), alkoxycarbonyl, and —$Si(R_f)_3$, wherein $R_f$ is selected independently of each other $R_f$ from alkyl and aryl. Preferred protecting groups are silyl protecting groups, such as triethylsilyl, t-butyldimethylsilyl, t-butyldiphenylsilyl, triisopropylsilyl, and the like.

Azide reducing agents include organophospines, such as trialkylphosphine, triarylphosphine, and tri(alkyl/aryl)phosphine (or mixtures thereof), more preferably trimethyl phosphine, triethyl phosphine, tributyl phosphine, triphenyl phosphine, tricyclohexylphosphine, tris(4-methoxyphenyl)-phosphine and/or tripropyl phosphine, and/or mixtures thereof.

"Suitable solvent" as used herein is intended to refer to a single solvent as well as mixtures of solvents. Solvents may be selected, as appropriate for a given reaction step, from, for example, aprotic polar solvents such as DMF, DMA, DMSO, dimethylpropyleneurea, N-methylpyrrolidone, and hexamethylphosphoric triamide; ether solvents such as diethyl ether, THF, 1,4-dioxane, methyl t-butyl ether, dimethoxymethane, and ethylene glycol dimethyl ether; alcohol solvents such as MeOH, EtOH, and isopropanol; and halogen-containing solvents such as methylene chloride, chloroform, carbon tetrachloride, and 1,2-dichloroethane.

"Polar solvents" are those solvents that have dipole moments and are capable of dissolving ionic compounds or covalent compounds that ionize. For example, polar solvents herein may include water, acetonitrile, 1-methyl-2-pyrrolidinone (NMP), N,N-dimethylacetamide (DMA), N,N-dimethylformamide (DMF), tetrahydrofuran (THF), and alcohols (such as MeOH, EtOH, IPA, tert-butanol, and the like), and mixtures thereof. Preferred are polar solvents comprising acetonitrile, water, EtOH, and mixtures thereof.

Reduced temperature herein means temperatures below room temperature (i.e., below about 25° C.), preferably at temperatures below about 10° C., and more preferably at temperatures below about 0° C. One skilled in the field will recognize that the temperature selected for any particular reaction step may be limited by the choice of solvents or other reagents used in the particular step (e.g., by their freezing points).

The terms "alkyl" and "alk" whether alone or in combination with some other group, refer to a straight or branched chain alkane (hydrocarbon) radical attached at any available carbon atom, containing from 1 to 10 carbon atoms, preferably 1 to 6 carbon atoms, more preferably from 1 to 4 carbon atoms. Exemplary such groups include, but are not limited to methyl, ethyl, propyl, isopropyl, n-butyl, t-butyl, isobutyl, pentyl, hexyl, heptyl, 4,4-dimethylpentyl, octyl, 2,2,4-trimethylpentyl, and the like. "Lower alkyl" or "lower alkylene"

means a straight or branched chain alkyl having one to four carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms, and the term "$C_{1-4}$alkyl" means alkyl groups of 1 to 4 carbon atoms.

The term "alkylene" refers to a bivalent hydrocarbon radical, as described above for "alkyl" but with two points of attachment. For example, a methylene group is a —$CH_2$— group and an ethylene group is a —$CH_2$—$CH_2$— group.

When the term alkyl is used in connection with another group, as in heterocycloalkyl or cycloalkylalkyl, this means the other identified (first named) group is bonded directly through an alkyl group as defined above (e.g., which may be branched or straight chain). Thus, the term "alkyl" is used in this instance to refer to an alkylene, e.g., a divalent alkyl group, having two available points of attachment. For example, cyclopropyl$C_{1-4}$alkyl means a cyclopropyl group bonded through a straight or branched chain alkylene having one to four carbon atoms, and hydroxyalkyl means the group OH bonded through a straight or branched chain alkylene having one to ten carbon atoms, preferably 1 to 6 carbon atoms, more preferably 1 to 4 carbon atoms. In the case of substituents, as in "substituted cycloalkylalkyl," the alkylene portion of the group, besides being branched or straight chain, may be substituted as recited below for substituted alkyl groups and/or the first named group (e.g., cycloalkyl) may be substituted as recited herein for that named group (e.g., cycloalkyl).

"Substituted alkyl" refers to an alkyl group substituted with one or more substituents, preferably 1 to 4 substituents, at any available point of attachment. However, when an alkyl group is substituted with multiple halo substituents, the alkyl may contain as valence allows up to 10 substituents, more preferably up to seven substituents. Alkyl substituents may include one or more of the following groups: halo (e.g., a single halo substituent or multiple halo substituents forming, in the latter case, groups such as a perfluoroalkyl group or an alkyl group bearing $Cl_3$ or $CF_3$), cyano, —$OR_a$, —$SR_a$, —$C(=O)R_a$, —$C(=O)OR_a$, —$OC(=O)R_a$, —$OC(=O)OR_a$, —$NR_aR_b$, —$C(=O)NR_aR_b$, —$OC(=O)NR_aR_b$, —$S(=O)R_a$, —$S(O)_2 R_a$, —$NHS(O)_2R_a$, —$NHS(O)_2NHR_a$, —NHC(=O)$NHR_a$, —NHC(=O)$R_a$, —NHC(O)$_2R_a$, —NHC(=N—CN)$R_a$, aryl, heterocycle, cycloalkyl, and/or heteroaryl, wherein the groups $R_a$ and $R_b$ are independently selected from hydrogen, alkyl, alkenyl, cycloalkyl, heterocyclo, aryl, and heteroaryl, and wherein each $R_a$ and/or $R_b$ in turn is optionally substituted with one to four groups selected from alkyl, alkenyl, halogen, haloalkyl, haloalkoxy, cyano, nitro, amino, alkylamino, aminoalkyl, hydroxy, hydroxyalkyl, alkoxy, thiol, alkylthio, phenyl, benzyl, phenyloxy, benzyloxy, $C_{3-7}$cycloalkyl, five or six membered heterocyclo or heteroaryl, and/or a lower alkyl or lower alkenyl substituted with one to four groups selected from hydroxy, cyano, halogen, halo$C_{1-4}$alkyl, halo$C_{1-4}$alkoxy, cyano, nitro, amino, $C_{1-4}$alkylamino, amino$C_{1-4}$alkyl, hydroxy$C_{1-4}$alkyl, $C_{1-4}$alkoxy, thiol, and/or $C_{1-4}$alkylthio. For the avoidance of doubt, a "substituted lower alkyl" means an alkyl group having one to four carbon atoms and one to four substituents selected from those recited immediately above for substituted alkyl groups. In the case of a substituted lower alkyl, preferably the groups $R_a$ and $R_b$ are selected from hydrogen, lower alkyl, lower alkenyl, $C_{3-7}$cycloalkyl, phenyl, and five to six membered monocyclic heterocyclo and/or heteroaryl, in turn optionally substituted as above.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include alkyl, substituted alkyl, and those groups recited above as alkyl substituents.

The terms "alkoxy" and "alkylthio" refer to an alkyl group as described above bonded through an oxygen linkage (—O—) or a sulfur linkage (—S—), respectively. The terms "substituted alkoxy" and "substituted alkylthio" refer to a substituted alkyl group as described above bonded through an oxygen or sulfur linkage, respectively. A "lower alkoxy" or a $C_{1-4}$alkoxy is a group OR, wherein R is lower alkyl (alkyl of 1 to 4 carbon atoms).

"Amino" is $NH_2$. An alkylamino is —$NR_cR_d$ wherein at least one of $R_c$ and $R_d$ is an alkyl or substituted alkyl, and the other of $R_c$ and $R_d$ is selected from hydrogen, alkyl, and substituted alkyl. An "aminoalkyl" means an amino group bonded through an alkylene group (-alkylene-$NH_2$), and an alkylaminoalkyl means an alkylamino as defined above bonded through an alkylene group (-alkylene-$NR_cR_d$).

The term "aryl" refers to cyclic, aromatic hydrocarbon groups which have 1 to 3 aromatic rings, especially monocyclic or bicyclic groups such as phenyl or naphthyl. Aryl groups which are bicyclic or tricyclic must include at least one fully aromatic carbocyclic ring but the other fused ring or rings may be aromatic or non-aromatic and may optionally contain heteroatoms, provided that in such cases the point of attachment will be to the aromatic carbocyclic ring. Additionally, when an aryl group has fused thereto a heterocyclic or cycloalkyl ring, the heterocyclic and/or cycloalkyl ring may have one or more carbonyl carbon atoms, i.e., attached via a double bond to an oxygen atom to define a carbonyl group. Thus, examples of "aryl" may include without limitation:

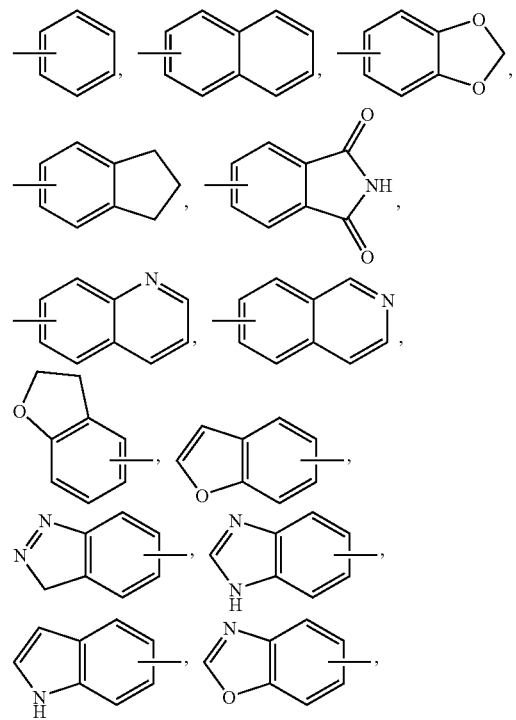

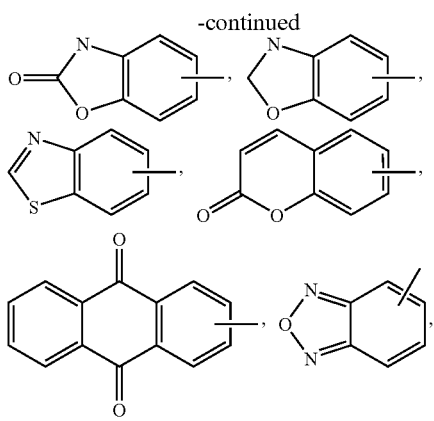

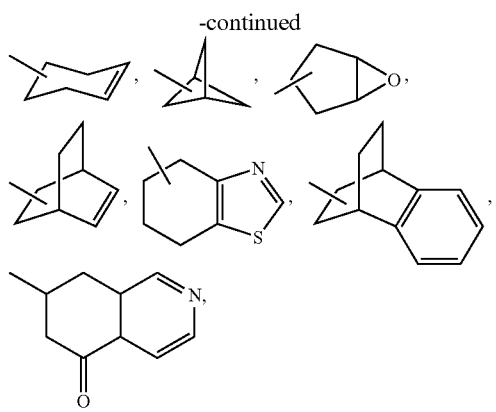

and the like.

The term "arylene" refers to a bivalent aryl radical, i.e., an aryl group as defined above having two points of attachment to two other groups, at any available points of attachment of the aryl ring. Arylene rings may also be substituted with any of the groups suitable for substitution on the aryl groups defined herein.

"Substituted aryl" refers to an aryl or arylene group as defined above substituted by one or more substituents, preferably 1 to 4 substituents, at any point of attachment. Substituents include alkyl, substituted alkyl, alkenyl, substituted alkenyl, as well as those groups recited above as alkyl substituents.

The term "carbocyclic" means a saturated or unsaturated monocyclic, bicyclic, or tricyclic ring (preferably mono- or bicyclic) in which all atoms of all rings are carbon. Thus, the term includes cycloalkyl and aryl rings. The carbocyclic ring may be substituted in which case the substituents are selected from those recited above for cycloalkyl and aryl groups.

The term "cycloalkyl" refers to a fully saturated or partially saturated cyclic hydrocarbon group containing from 1 to 3 rings and 3 to 7 carbon atoms per ring. Exemplary fully saturated cycloalkyl groups include cyclopropyl, cyclobutyl, cyclopentyl, and cyclohexyl. Exemplary partially saturated cycloalkyl groups include cyclobutenyl, cyclopentenyl, and cyclohexenyl. The term "cycloalkyl" includes such groups having a bridge of three to four carbon atoms. Additionally, cycloalkyl groups which are bicyclic or tricyclic must include at least one fully saturated or partially saturated hydrocarbon ring but the other fused ring or rings may be aromatic or non-aromatic and may contain heteroatoms, provided that in such cases the point of attachment will be to the cyclic, non-aromatic hydrocarbon group. Additionally, one or more carbon atoms of the cycloalkyl group may form a carbon-to-oxygen double bond to define a carbonyl group. Thus, examples of "cycloalkyl" groups may include, without limitation:

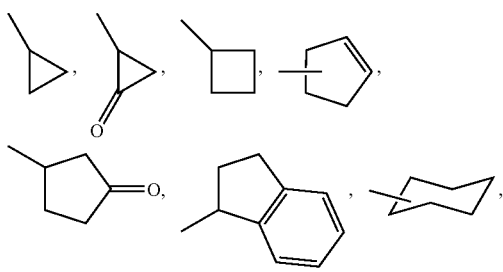

and the like.

The term "cycloalkylene" refers to a bivalent cycloalkyl radical, i.e., a cycloalkyl group as defined above having two points of attachment to two other groups, at any available two points of attachment of the cycloalkyl ring.

"Substituted cycloalkyl" refers to a cycloalkyl group as defined above substituted at any available point of attachment with one or more substituents, preferably 1 to 4 substituents. Cycloalkyl substituents include alkyl, substituted alkyl, alkenyl, substituted alkenyl, and those groups recited above as alkyl substituents.

The term "guanidinyl" means the group

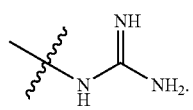

Thus, a guanidinylalkyl means an alkyl group bonded to the guanidinyl such as a group having the formula,

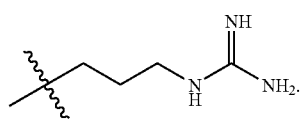

The term "halogen" or "halo" refers to fluorine, chlorine, bromine and iodine.

The term "heteroatoms" includes oxygen, sulfur and nitrogen.

The term "haloalkyl" means an alkyl having one or more halo substituents, including without limitation groups such as —$CH_2F$, —$CHF_2$ and —$CF_3$.

The term "haloalkoxy" means an alkoxy group having one or more halo substituents. For example, "haloalkoxy" includes —$OCF_3$.

When the term "unsaturated" is used herein to refer to a ring or group, the ring or group may be fully unsaturated or partially unsaturated.

The term "heteroaryl" refers to an aromatic group which is a 4 to 7 membered monocyclic, 7 to 11 membered bicyclic, or 10 to 15 membered tricyclic ring system, which has at least one ring containing at least one heteroatom. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom.

The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic and may be carbocyclic, provided that in such cases the point of attachment will be at any available nitrogen or carbon atom of an aromatic heteroatom-containing ring. Additionally, the definition of heteroaryl groups itself includes rings wherein one or more of the carbon atoms is attached via a double bond to an oxygen atom to define a carbonyl group (provided the heteroaryl group is aromatic) and also when a heteroaryl group has fused thereto a heterocyclic or cycloalkyl ring, the heterocyclic and/or cycloalkyl ring may have one or more carbonyl groups.

Exemplary monocyclic heteroaryl groups include pyrrolyl, pyrazolyl, pyrazolinyl, imidazolyl, oxazolyl, isoxazolyl, thiazolyl (i.e., (i.e., 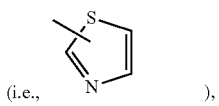 ), thiadiazolyl, isothiazolyl, furanyl, thienyl, oxadiazolyl, pyridyl, pyrazinyl, pyrimidinyl, pyridazinyl, triazinyl and the like. Additionally, since the definition of heteroaryl groups itself includes rings wherein one or more of the carbon atoms defines a carbonyl group, rings such as 2,4-dihydro-[1,2,4]triazol-3-one (i.e., (i.e., 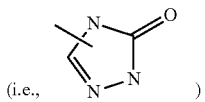 )

and the like are included.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heteroalkylene" refers to a bivalent heteroaryl radical, i.e., a heteroaryl group as defined above having two points of attachment to two other groups, at any available two points of attachment of the heteroaryl ring.

"Substituted heteroaryl" groups are heteroaryl groups as defined above substituted with one or more substituents, preferably 1 to 4 substituents, at any available point of attachment. Exemplary substituents include, but are not limited to alkyl, substituted alkyl, alkenyl, substituted alkenyl, as well as those groups recited above as alkyl substituents.

The terms "heterocycle", heterocyclic" and "heterocyclo" are used interchangeably and each refer to a fully saturated or partially unsaturated non-aromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. Heterocyclic groups which are bicyclic or tricyclic must include at least one non-aromatic non-carbocyclic ring, but the other fused ring or rings may be aromatic or non-aromatic and may be carbocyclic, provided that in such cases the point of attachment will be at any available nitrogen or carbon atom of a non-aromatic heteroatom-containing ring. Additionally, the definition of heterocyclic groups itself includes rings wherein one or more of the carbon atoms is attached via a double bond to an oxygen atom to define a carbonyl group (provided the heterocyclic group is non-aromatic) and also when a heterocyclic group has fused thereto a further ring, such further ring may have one or more carbonyl groups.

Exemplary monocyclic heterocyclic groups include pyrrolidinyl, imidazolidinyl, tetrahydrofuryl, piperidinyl, piperazinyl, pyrazolidinyl, imidazolinyl, pyrrolinyl, tetrahydropyranyl, morpholinyl, thiamorpholinyl, and the like.

"Substituted heterocycle," "substituted heterocyclic," and "substituted heterocyclo" refer to heterocycle, heterocyclic, or heterocyclo groups as defined above substituted with one or more substituents, preferably 1 to 4 substituents, at any available point of attachment. Exemplary substituents include alkyl, substituted alkyl, alkenyl, substituted alkenyl, as well as those groups recited above as exemplary alkyl substituents.

"Hydroxy" or "hydroxyl" refers to —OH.

"Thiol" means the group —SH.

The term "folate-binding moiety or analog or derivative thereof" as used herein means a moiety that will bind to a folate-receptor protein (not a monoclonal antibody) that is overexpressed or preferentially expressed on cancer cells. For example, it is known that the folate receptor (FR) is overexpressed in ovarian cancer cells and other cancer cells. Illustrative analogs and derivatives of folate are disclosed in U.S. Pat. App. Pub. No. 2005/0002942 to Vlahov et al., (hereinafter "Vlahov").

The term "releasable linker" as used herein means a bivalent linker that includes at least one cleavable bond that can be broken under physiological conditions (e.g., a pH-labile, reductively-labile, acid-labile, oxidatively-labile, or enzyme-labile bond.) It should be appreciated that such physiological conditions resulting in bond breaking include standard chemical hydrolysis reactions that occur, for example, at physiological pH, or as a result of compartmentalization into a cellular organelle, such as an endosome having a lower pH than cytosolic pH, or as a result of reaction with a cellular reducing agent such as glutathione.

It is understood that a cleavable bond can connect two adjacent atoms within the releasable linker and/or connect other groups to the releasable linker such as Q and K, as described herein, at either or both ends of the linker.

The term "quaternary nitrogen" refers to a tetravalent positively charged nitrogen atom including, for example, the positively charged nitrogen in a tetraalkylammonium group (e.g., tetramethylammonium or N-methylpyridinium), the positively charged nitrogen in protonated ammonium species (e.g., trimethylhydroammonium or N-hydropyridinium), the positively charged nitrogen in amine N-oxides (e.g., N-methyl-morpholine-N-oxide or pyridine-N-oxide), and the positively charged nitrogen in an N-amino-ammonium group (e.g., N-aminopyridinium).

General Methods

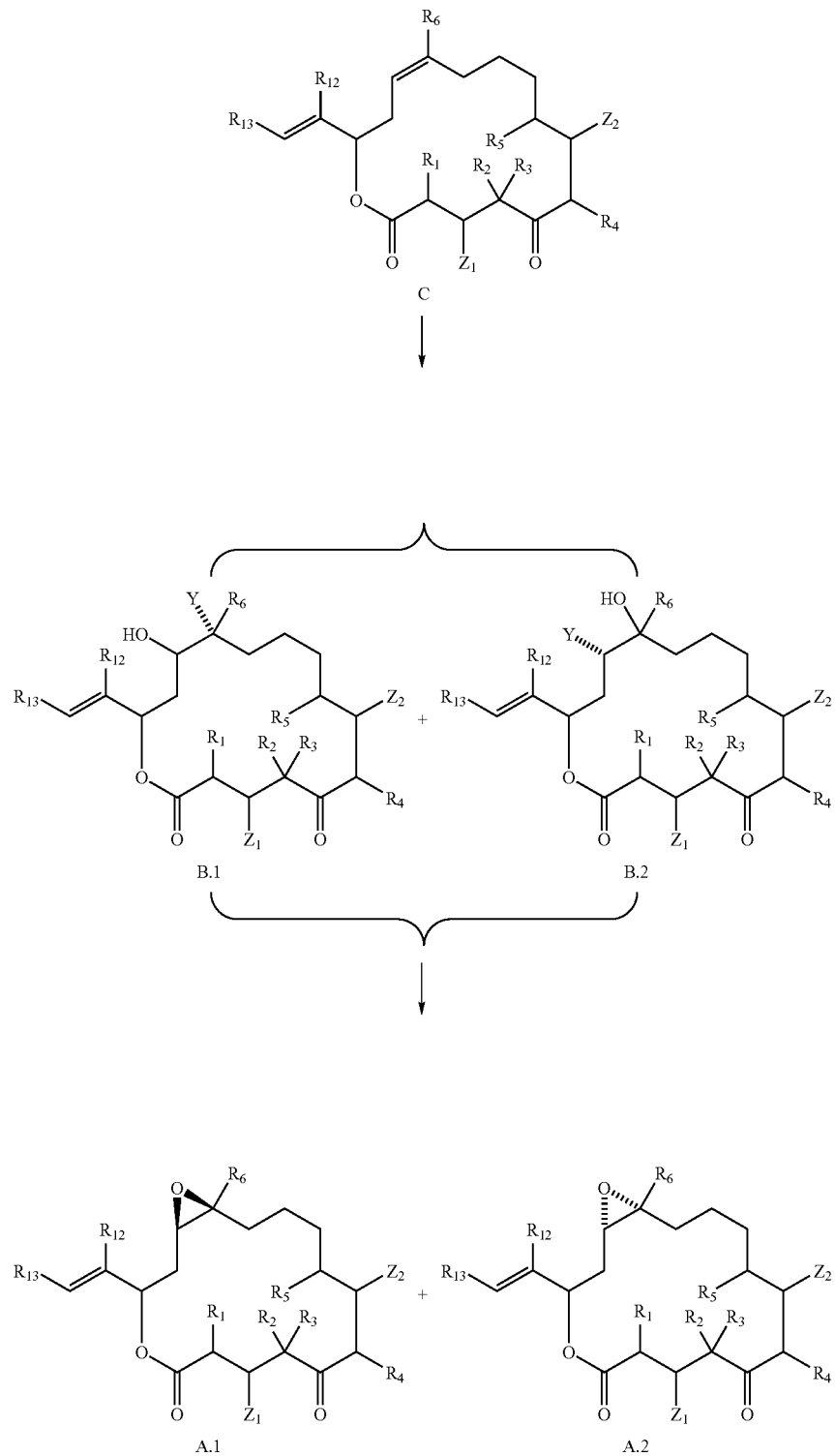

Scheme 1 illustrates an embodiment of the present invention process for making compounds of formula A.1 and A.2 from a compound of formula C, with stereoselective preference for compounds of formula A.1, wherein the various groups $R_1$, $R_2$, $R_3$, $R_4$, $R_5$, $R_6$, $R_{12}$, $R_{13}$, $Z_1$ and $Z_2$, are as otherwise defined herein (e.g., including in the Summary of Invention and alternate embodiments). Compounds of formula C are known and can be obtained by methods well known in the field, for example, by fermentation (see, e.g., Gerth et al., "Studies on the Biosynthesis of Epothilones: The Biosynthetic Origin of the Carbon Skeleton," *Journal of Antibiotics*, 53(12):1373-1377 (December 2000); Hofle et al., "Epothilone A and B-Novel 16-Membered Macrolides: Isolation, Crystal Structure, and Conformation in Solution", *Angew. Chem. Int. Ed. Engl.*, 35(13/14):1567-1569 (1996); see also WO 03/072730, U.S. Pat. No. 6,410,301; U.S. Pat. No. 6,303,342; and US 2002/0137152A1) the disclosures of which are herein incorporated by reference) or by total or semi-synthesis (see, e.g., Vite et al. U.S. Pat. Nos. 6,605,599; 6,242,469; 6,867,333, U.S. Pat. Appl. Pub. 2006/004065, the disclosures of which directed to methods of making are herein incorporated by reference). For example, a compound of formula C where $R_1$ is hydrogen, $R_2$, $R_3$, $R_4$, $R_5$, and $R_{12}$ are methyl, $Z_1$ and $Z_2$ are hydroxyl, $R_1$ is hydrogen and $R_{12}$ is 2-methylthiazol-4-yl, is epothilone C where $R_6$ is hydrogen, and epothilone D where $R_6$ is methyl, both obtainable from fermentation of *Sorangium cellulosum*. A compound of formula C wherein $Z_1$ and $Z_2$ are protected, e.g., comprise groups of formulae $OR_p$, are known and can be readily obtained by methods well known in the art. See, e.g., WO 93/10121; DE 19542986A1; WO 97/19086; WO 98/22461; see also U.S. Pat. Nos. 6,369,234, and 6,972,335. One such approach involves treatment with chlorotriethylsilane in the presence of base such as Hunig's base to afford a protected compound wherein $R_p$ is triethylsilane. See also Cooper, B., "Silylation as a Protective Method In Organic Synthesis," *Chemistry & Industry*, 20:794-797 (1978); Lalonde, et al., "Use of Organosilicon Reagents As Protective Groups In Organic Synthesis," *Synthesis*, 9:817-845 (1985); and Olsson, "Silicon-Based Protective Groups in Organic Synthesis," *Acta Pharmaceutical Suecica*, 23(6):370-385 (1986).

Halohydrins of formulae B.1 and B.2 (Y is Cl, Br, or I) can be prepared from a compound of formula C by treatment with a halogenating agent. For example, electrophilic addition in polar solvents using halogen ($Y_2$) (preferably, Y=iodine) can stereoselectively provide regioisomeric halohydrins of formulae B.1 and B.2, where Y is halogen (preferably iodine). Alternatively N-halo succinimides can also be used for the same transformation, such as N-chlorosuccinimide (NCS), N-bromosuccinimide (NBS), or N-iodosuccinimide (NIS). Polar solvents for this step may include acetonitrile, water, NMP, DMA, DMF, THF, and alcohols (e.g., MeOH, EtOH, IPA, tert-butanol, and the like), and mixtures thereof, and preferably comprise acetonitrile, water, EtOH, and mixtures thereof, and more preferably acetonitrile.

Preferably the step of halogenating the epothilone compound of formula C is performed at reduced temperatures, preferably at temperatures below 10° C., more preferably at temperatures below 0°, more preferably at temperatures between about 0° C. and −15° C., and most preferably at temperatures in the range of about −5° C. to −10° C.

Additionally, preferably excess halogenating reagent is used in this step followed by a quenching agent to remove the excess. For example, halogenating reagent may be added at a molar ratio of 2 to 5 (halogenating agent) to 1:Compound C, more preferably about 5:1 (halogenating agent: Compound C) (molar ratio) followed by quenching with quenching agents well known in the field. For example, quenching agents may be used as disclosed in March, *Advanced Organic Chemistry, Reactions, Mechanisms and Structures*, J. Wiley & Sons, New York, p. 813 (1992) and references cited therein; and Zanger, M. et al., *J. Org. Chem.*, 40:248 (1975), both incorporated herein by reference with regard to their disclosures of quenching agents. As a non-limiting example, 15% sodium metabisulfite solution may be used.

Ring-closure of compounds of formulae B.1 and B.2, to form the epoxide epothilone compounds of formula A.1 and A.2 then proceeds in the presence of base. Inventors herein have discovered that with this reaction, it is not necessary to isolate or separate the intermediates B.1 and B.2 but rather, upon adding base, both intermediates will convert to compounds of formula A.1 and A.2 with stereoselective preference for compounds of formula A.1. Accordingly, desirable ratios of compound A.1 to A.2 can be achieved, e.g., of more than 2:1, even more than 5:1, and even greater than 9:1. Bases may be selected from those described above, and preferred bases for this conversion are tertiary amines such as N-methylmorpholine, triethylamine, and diisopropylethylamine (a/k/a/ Hunig's base), more preferably triethylamine or Hunig's base. Preferably, the reaction is performed in a polar solvent including a polar/aqueous solvent system. Polar solvents may include those described above, and preferred are acetonitrile, water, EtOH, and mixtures thereof, more preferably acetonitrile/water.

Additionally, the reaction of converting B.1 and B.2 to A.1 and A.2 is preferably performed at elevated temperatures which speeds the reaction. One skilled in the field will recognize the elevated temperature will be limited by the choice of solvent, and the temperatures/solvent system can be optimized accordingly. For example, where acetonitrile/water is used, preferably the reaction is performed at a temperature of about 40° C. to 60° C., more preferably at about 50° C. to 60° C. Compounds of formula A.1 can be converted to aziridinyl epothilones having stereospecifity aligned with the major natural epothilones (e.g., epothilones A, B, C, D, etc.), by methods known in the field (e.g., as described in Regueiro-Ren et al., *Organic Letters*, 3:2693-2696 (2001)) or more preferably, as otherwise shown herein, e.g., in Schemes 2 and 3 and the examples that follow.

Scheme 1.1

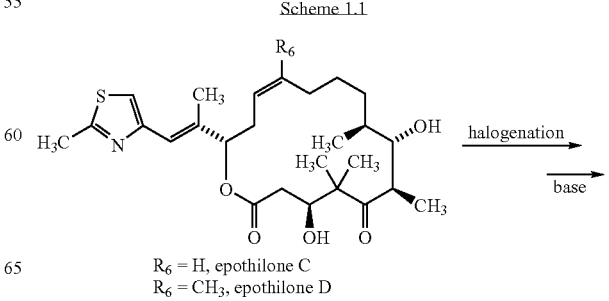

$R_6$ = H, epothilone C
$R_6$ = $CH_3$, epothilone D

-continued

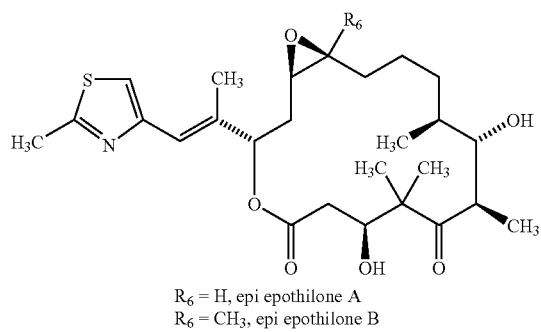

$R_6$ = H, epi epothilone A
$R_6$ = $CH_3$, epi epothilone B

Scheme 1.1 shows an example of directly converting compounds of formula C, illustrated here as epothilones C/D, into compounds of formula A.1, illustrated here as epi-epos A/B, without proceeding through intermediate protecting groups. Following the general conditions illustrated in Scheme 1, the epothilone C and/or D compound(s) is treated with a halogenating agent, preferably in polar solvent at reduced temperature, and preferably with excess halogenating agent followed by quenching, and then, intermediate halohydrin compounds thereby obtained (which need not be isolated or purified), are treated with base, preferably at elevated temperature in a polar/aqueous solvent system, to provide epi-epothilones A/B, in high yield as compared with the diastereoisomers epothilones A/B.

Scheme 2

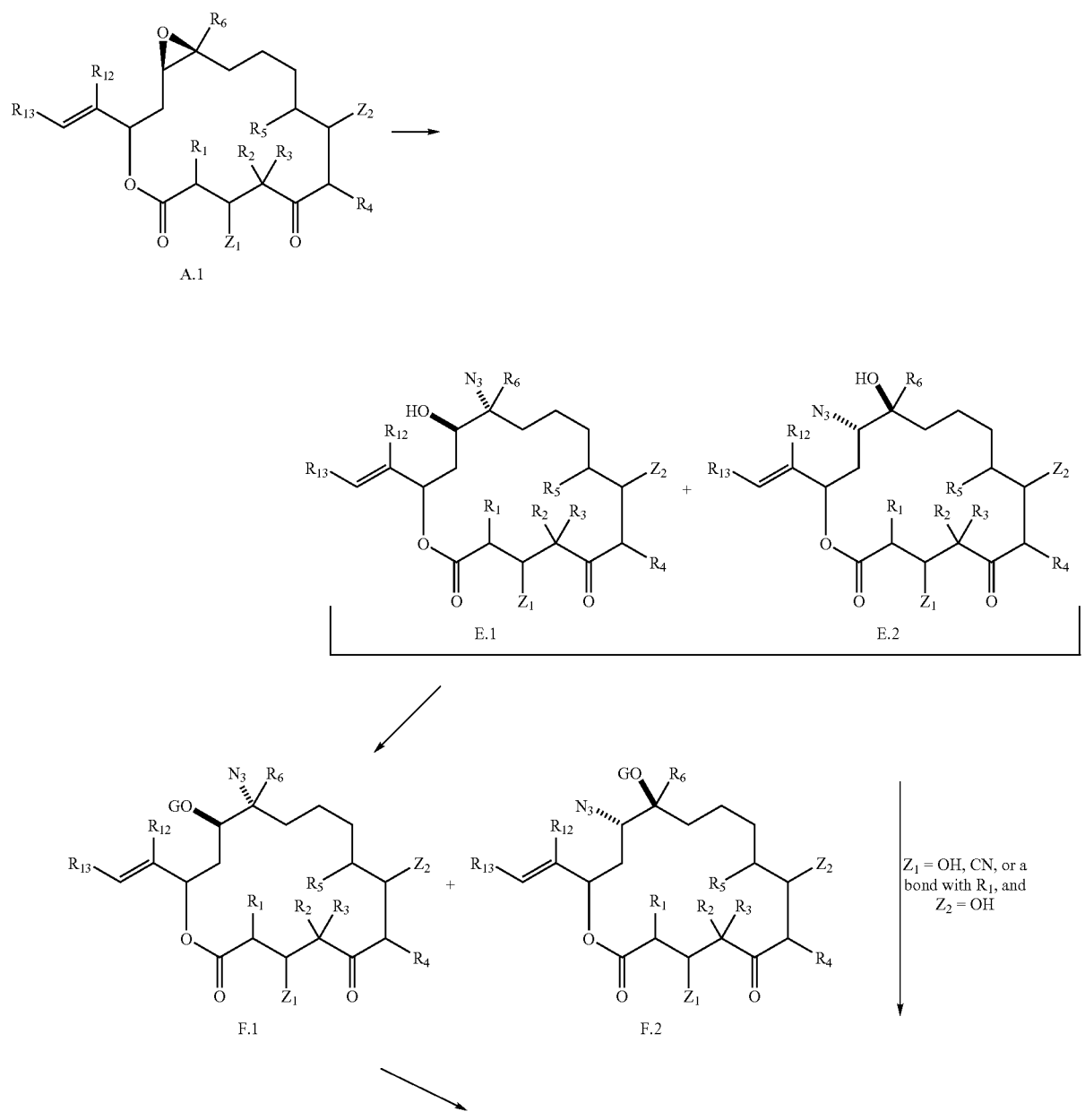

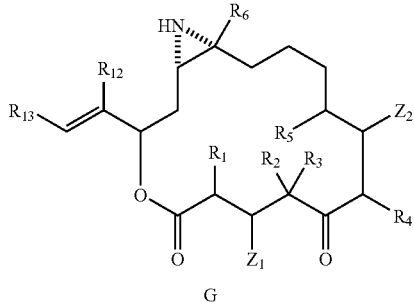

G

Scheme 2 shows an example of converting compounds of formula A.1 into aziridinyl-epothilone compounds having formula G. In compounds of formula A.1, the groups $Z_1$ and/or $Z_2$ may by hydroxyl and also may comprise protecting groups, e.g., at least one of $Z_1$ and/or $Z_2$ may be a group $OR_p$. In either case, a compound of formula A.1 can be transformed into the azido-alcohols of formulae E.1 and E.2 by azide displacement in the presence of an azide donor such as inorganic azide salts or tetra-alkyl ammonium azides in alcoholic solvents. Advantageously, an ammonium salt such as an ammonium halide (ammonium chloride, ammonium bromide) is used in conjunction with the azide donor to increase solubility of the azide and accelerate the reaction. Where $Z_1$=OH, CN, or a bond with $R_1$ and $Z_2$ is hydroxyl, preparation of compounds of formula G, preferably proceeds directly by reduction of the azido group with an azide reducing agent such as an organophosphine (e.g., trialkylphosphine, triarylphosphine, and tri(alkyl/aryl)phosphine, or mixtures thereof, more preferably trimethyl phosphine, triethyl phosphine, tributyl phosphine, triphenyl phosphine, tricyclohexylphosphine, tris(4-methoxyphenyl)-phosphine and/or tripropyl phosphine, and/or mixtures thereof, and even more preferably, triphenylphosphine) in polar solvents, more preferably, anhydrous polar solvents, such as anhydrous acetonitrile. Where $Z_1$ and/or $Z_2$ comprise protecting groups, it will be advantageous in preparing compounds of formula G, to minimize side product reactions and enhance yields, to first convert the $C_{12}$, $C_{13}$ hydroxyl groups to leaving groups OG as in compounds of formulae F.1 and F.2 (such as, for example, mesylate, tosylate, nosylate, triflate and the like), by methods known in the art, e.g., upon treatment with methanesulfonyl chloride and triethylamine in a suitable organic solvent such as dichloromethane. Compounds of F.1 and F.2 can be converted to compounds of formula G, by reduction with an azide reducing agent in a polar solvent, as above. Thus, where compounds of formula A.1 comprise epi-epo's A and/or B (as in Scheme 1.1), the aziridinyl compounds of formula G can be directly prepared by azide displacement followed by reduction of the azido group with an azide reducing agent such as an organophosphine in polar solvents. Preferably, the reaction of Scheme 2 is conducted at about room temperature, or at a temperature in the range of about 20° C. to 40° C., and is conducted in an anhydrous environment. Compounds of formula G can then be used to prepare further aziridinyl epothilone analogs, such as compounds of formula H or X, below, by methods known in the art (see, e.g., U.S. Pat. No. 6,800,653; and Regueiro-Ren et al., *Organic Letters*, 3:2693-2696 (2001)), or preferably as shown in Scheme 3.

Scheme 3

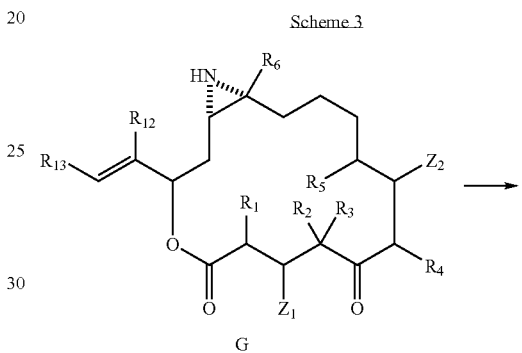

G

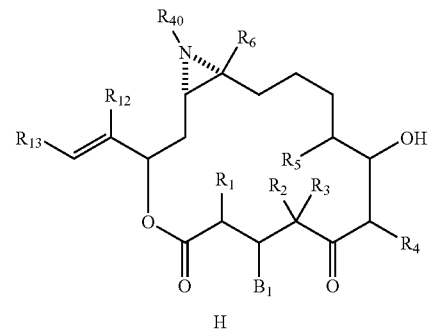

H

Scheme 3 illustrates an improved process of making aziridinyl analogs of formula H, from compounds of formula G, wherein the various groups $R_1$, $R_2$, $R_3$, $R_4$, $R_5$, $R_6$, $R_{12}$, $R_{13}$, $R_{40}$ and $B_1$, are as otherwise defined herein. This method is more simple and provides higher yields of substantially purified end products, as compared with previous methods, and also is more flexible with regard to use of protecting groups.

For instance, a compound of formula H can be prepared directly from a compound of formula G by treatment of the aziridine ring using a halide reagent $R_{40}$—Y, where Y is a halide, preferably with excess halide, in the presence of base. For example, compounds of formula H where $R_{40}$ is 2-hydroxyethyl, can be prepared upon treatment of the aziridine with 2-bromoethanol and a base such as a tertiary amine or potassium carbonate. Preferably the reaction is performed in a polar solvent, most preferably acetonitrile, at elevated temperature, e.g., preferably above 40° C., more preferably between about 50° C.-75° C., and most preferably between 70-75° C. Applicants have discovered the preferred ratio of halide to aziridinyl-epothilone for this reaction is about 5-7: halide to 1:formula G compound (molar ratio) to reduce impurities and improve yield, more preferably a ratio of 6:1 (halide:formula G compound) is used; higher ratios may produce greater impurities, and with lesser ratios (less halide), there are more incomplete reactions. Substantially pure crystalline compounds of formula H can be obtained with this process, e.g., with purities of above 90%, more preferably above 95%, and even more preferably at about 96-98% or 97 to 99%. Additionally, this process is flexible as protecting groups at $Z_1$ and/or $Z_2$ positions are not necessary, and if protecting groups are positioned on compounds of formula G, these protecting groups can be removed at any point of the reaction in converting compounds of formula G to those of formula H, using methods known in the art, for example, when $R_p$ is triethylsilyl, treatment with trifluoroacetic acid in dichloromethane effects deprotection to provide a compound of formula H.

Scheme 4

H-Cys(4-methoxytrityl)-2-chlorotrityl-Resin (loading 0.57 mmol/g)

1) Fmoc-Asp(OtBu)-OH, PyBOP, DIPEA, DMF then piperidine
2) Fmoc-Arg(Pbf)-OH, PyBOP, DIPEA, DMF, then piperidine
3) Fmoc-Asp(OtBu)-OH, PyBOP, DIPEA, DMF, then piperidine
4) Fmoc-Glu-OtBu, PyBOP, DIPEA, DMF, then piperidine
5) $N^{10}$TFA Pteroic Acid, PyBOP, DIPEA, DMSO
6) 92.5% TFA, 2.5% $H_2O$, 2.5% i-$Pr_3SiH$, and 2.5% ethanedithiol
7) $NH_4OH$ aq., then HCl aq.

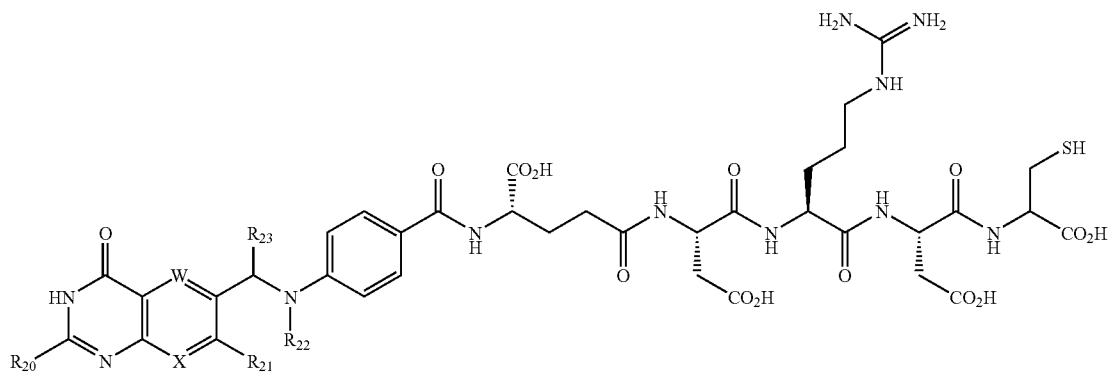

XI

Scheme 4 shows a process for making a folate analog or derivative V and bivalent linker T-Q having the formula XI, below, that may be used with compounds prepared using the invention to make conjugated molecules for targeted drug delivery, e.g., as per formula I, described further below. As shown in Scheme 4, a folate analog and bivalent linker can be assembled using methods known in the art, especially in the case where V is folic acid or a folic acid analog, as described, for example, by Jackson, et al., *Advanced Drug Delivery Rev.*, 56:1111-1125 (2004), the disclosure of which is herein incorporated by reference, and T-Q is a peptide. Sequential peptide coupling of a cysteine-loaded polystyrene resin with Fmoc-protected aspartate, arginine, aspartate, and then glutamate can be effected using PyBOP as coupling agent and piperidine as Fmoc-deprotection agent. $N^{10}$-Trifluoroacetamide-protected pteroic acid can be prepared in two steps by enzymatic (carboxypeptidase G) conversion of folic acid to pteroic acid, followed by $N^{10}$-protection using trifluoroacetic anhydride. Next, coupling of the $N^{10}$-protected pteroic acid to the resin-bound peptide followed by cleavage from the resin with trifluoroacetic acid and removal of the $N^{10}$-trifluoroacetyl group using ammonium hydroxide provides a V-T-Q fragment of a compound of formula I where V is folic acid and T-Q is -Asp-Arg-Asp-Cys-OH. Alternatively, pteroic acid analogs could be used in place of pteroic acid and other amino acids, could be used in place of those illustrated in Scheme 4.

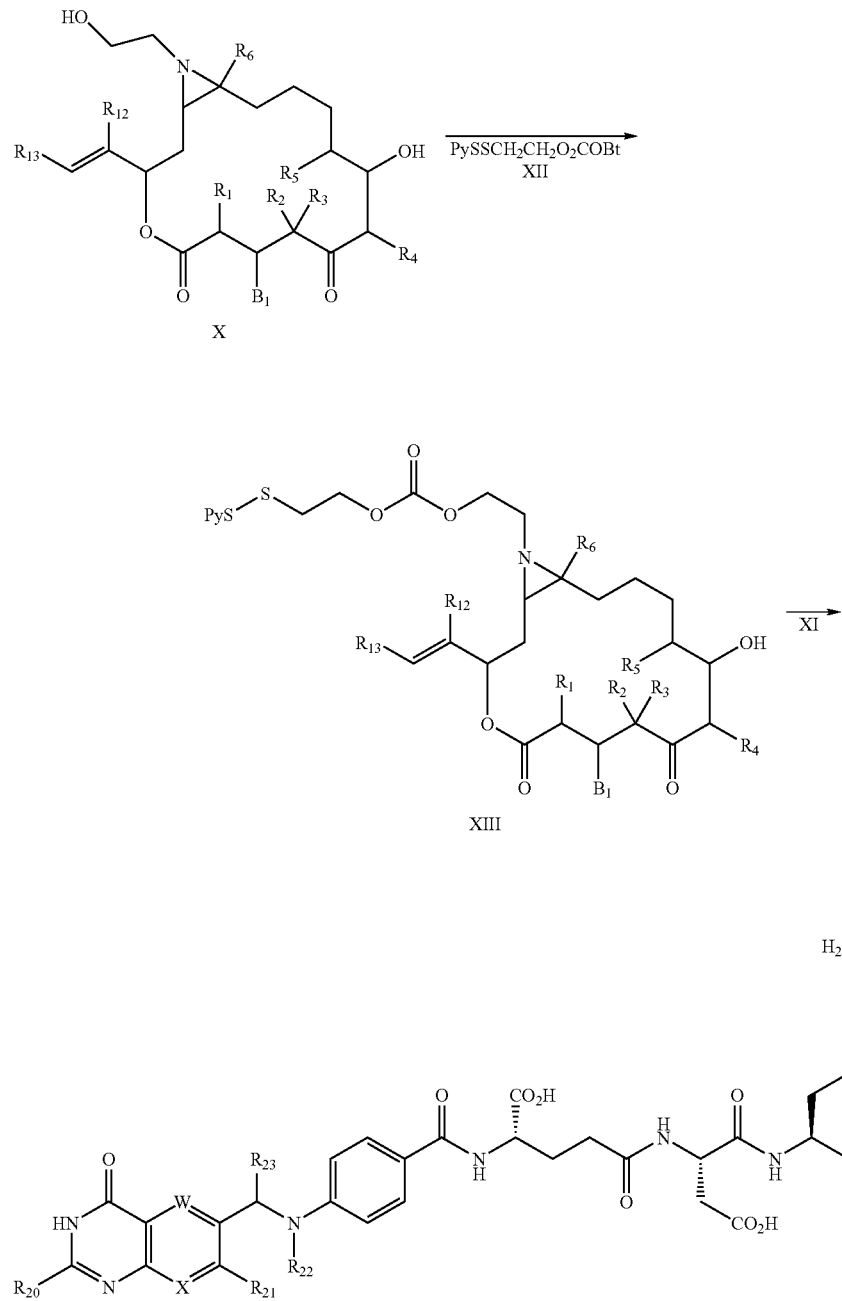

Scheme 5

-continued

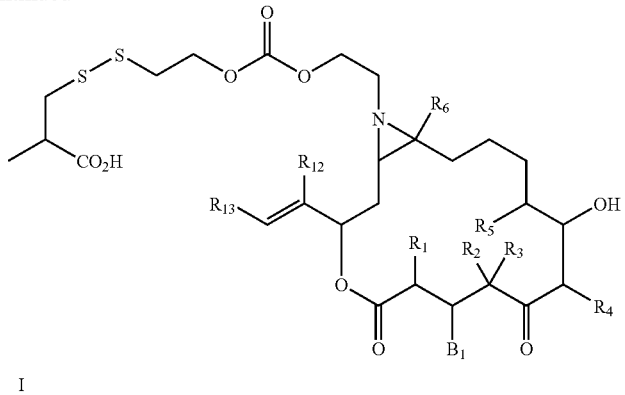

I

Scheme 5, above, shows a method for using the epothilone derivatives prepared according to the present invention to prepare a conjugated molecule of formula I, for use in targeted drug delivery. As shown in Scheme 5, assembly of compounds of formula I can be achieved by coupling compounds of formula X to a fragment V-T-Q by stepwise incorporation of a releasable linker M. By way of illustration, a compound of formula X where -A-K-His —CH$_2$CH$_2$OH can be converted to a disulfanylethyl carbonate XIII using an activated benzotriazole compound of formula XII. A compound of formula XII can be prepared from mercaptoethanol, methoxycarbonyl sulfenyl chloride, and an optionally substituted 2-mercaptopyridine to provide an intermediate 2-(2-pyridin-2-yl)disulfanyl)ethanol, which can then be converted to a compound of formula XII by treatment with diphosgene and an optionally substituted 1-hydroxybenzotriazole. Subsequent disulfide exchange with a peptidyl folate such as XI provides a compound of formula I where V is folic acid, T-Q is a -Asp-Arg-Asp-Cys-OH, M is —SCH$_2$CH$_2$O(C=O)—, A is —CH$_2$CH$_2$— and K is O, and R$_6$ is hydrogen or methyl.

EMBODIMENTS OF THE INVENTION

According to one embodiment of the invention, a process is provided comprising, (a) reacting a compound having the formula (C')

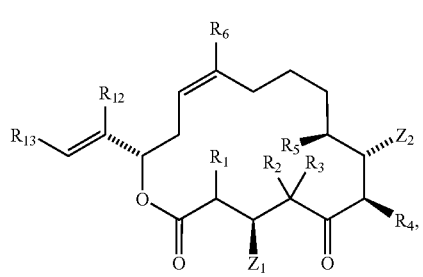

(C')

wherein,

R$_1$ is hydrogen or forms a bond with Z$_1$;

Z$_1$ is hydroxyl, cyano, is taken together with R$_1$ to form a bond, or is OR$_p$;

Z$_2$ is hydroxyl or OR$_p$; wherein R$_p$ is a protecting group;

R$_2$, R$_3$, and R$_5$ are, independently, hydrogen, alkyl, substituted alkyl, aryl or substituted aryl; or R$_2$ and R$_3$ may be taken together with the carbon to which they are attached to form an optionally substituted cycloalkyl;

R$_4$ is hydrogen, alkyl, alkenyl, alkynyl, substituted alkyl, aryl, or substituted aryl;

R$_6$ is hydrogen or alkyl;

R$_{12}$ is H, alkyl, substituted alkyl, or halogen; and

R$_{13}$ is aryl, substituted aryl, heteroaryl or substituted heteroaryl;

(b) with a halogenating reagent to provide compounds having the formulae (B.1') and (B.2'),

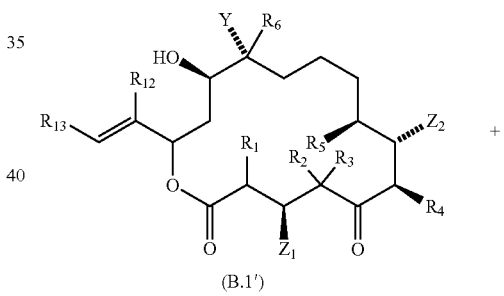

(B.1')

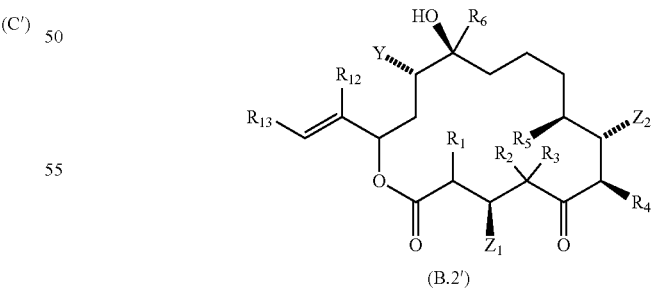

(B.2')

wherein Y is halogen, and R$_1$, R$_2$, R$_3$, R$_4$, R$_5$, R$_6$, R$_7$, R$_8$, R$_{12}$, R$_{13}$, Z$_1$ and Z$_2$ are as previously described; and (c) performing an epoxide ring closure of compounds of formula (B.1') and (B.2)' to provide compounds of formulae (A.1') and (A.2'), wherein compound of formula (A.1') is obtained in high yield,

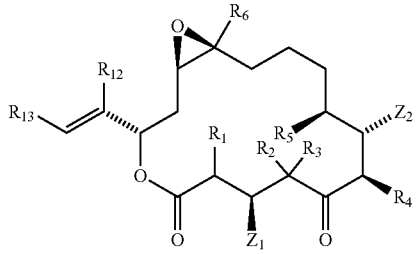

A.1'

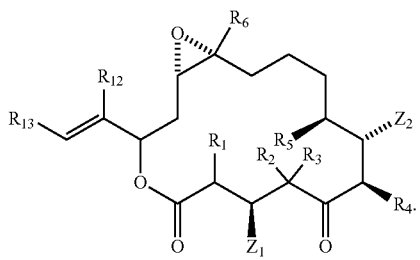

A.2'

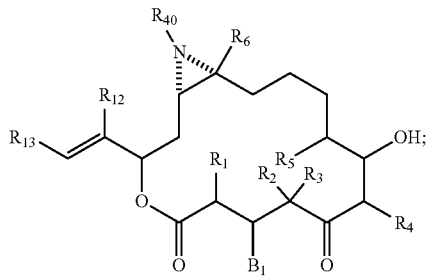

H

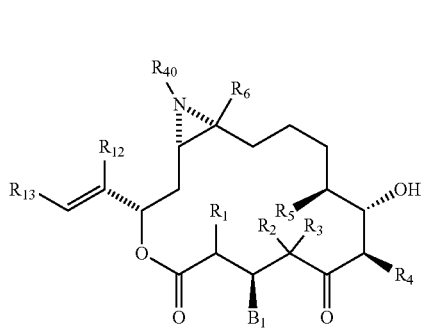

H'

In each of the alternative processes herein, preferably, $R_1$ is hydrogen.

In each of the alternative processes herein, preferably, $Z_1$ and $Z_2$ are hydroxyl, and the reaction proceeds without any protecting groups, but where $Z_1$ and $Z_2$ are selected from $OR_p$; preferably $R_p$ is a protecting group selected from alkyl, substituted alkyl (such as alkoxy alkyl, aryloxyalkyl), alkoxycarbonyl, and —Si$(R_f)_3$, wherein $R_f$ is selected independently of each other $R_f$ from alkyl and aryl; even more preferred protecting groups are silyl protecting groups, such as triethylsilyl (TES), t-butyldimethylsilyl, t-butyldiphenylsilyl, and triisopropylsilyl, more preferably TES.

In each of the alternative processes herein, preferably $R_2$, $R_3$, and $R_5$ are, independently, hydrogen or lower alkyl, more preferably methyl.

In each of the alternative processes herein, preferably $R_4$ is hydrogen, alkyl, alkenyl, or alkynyl, more preferably lower alkyl, lower alkenyl, or lower alkynyl, more preferably methyl.

In each of the alternative processes herein, preferably $R_6$ is hydrogen or alkyl, more preferably hydrogen or methyl.

In each of the alternative processes herein, preferably $R_{12}$ is H, lower alkyl, or halogen, more preferably halogen or methyl, most preferably methyl.

In each of the alternative processes herein, preferably $R_{13}$ is an optionally substituted 5 or 6 membered heteroaryl, more preferably optionally-substituted thiazolyl, pyridyl, or oxazolyl, and most preferably 2-methyl-4-thiazolyl.

Any one of the above preferred selections, or any combinations of the above preferred selections, may be selected for any of the processes recited herein, where such radicals appear.

The processes of the instant invention may be used to make aziridinyl-epothilone compounds as described in U.S. Pat. No. 6,800,653, U.S. Pat. No. 6,399,638 B1, and/or U.S. application Ser. No. 11/753,785, (US2007/0276018A1, published 29 Nov. 2007) filed concomitantly herewith, claiming priority to U.S. provisional application 60/808,366, filed May 25, 2006, all three of which patents and applications are incorporated herein by reference.

According to one embodiment, the present invention processes are used for making compounds having the Formula H, particularly compounds having the stereospecific form according to Formula H':

including pharmaceutically-acceptable salts and/or solvates thereof, wherein, $R_{40}$ is aryl, substituted aryl, heterocyclo, substituted heterocyclo, cycloalkyl, substituted cycloalkyl, or the group H—$K_1$-$A_1$-;

$K_1$ is absent or is —O—, —S—, or —$NR_7$—, $A_1$ is —$(CR_8R_9)_r$—$(CH_2)_s$—Z, wherein Z is —$(CHR_{10})$—, —C(=O)—, —C(=O)—C(=O)—, —OC(=O)—, —N($R_{11}$)C(=O)—, —SO$_2$—, or —N($R_{11}$)SO$_2$—;

$B_1$ is hydroxyl or cyano and $R_1$ is hydrogen or $B_1$ and $R_1$ are taken together to form a double bond;

$R_2$, $R_3$, and $R_5$ are, independently, hydrogen, alkyl, substituted alkyl, aryl or substituted aryl; or $R_2$ and $R_3$ may be taken together with the carbon to which they are attached to form an optionally substituted cycloalkyl;

$R_4$ is hydrogen, alkyl, substituted alkyl, alkenyl, alkynyl, aryl, or substituted aryl;

$R_6$ is hydrogen, alkyl or substituted alkyl;

$R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen;

$R_{13}$ is aryl, substituted aryl, heteroaryl or substituted heteroaryl; and r and s are each independently selected from 0 to 6. One skilled in the field will make selections from the radicals above to provide stable compounds and moieties, for example, when $K_1$ is —O— or —S—, and Z is —C(=O)—C(=O)—, —N($R_{11}$)C(=O)—, —SO$_2$—, or —N($R_{11}$)SO$_2$—; both of r and s preferably are not zero, and one when $K_1$ is —$NR_7$—, and Z is —C(=O)—C(=O)—, both of r and s preferably are not zero; and so forth.

In another embodiment, processes of the invention are applied in the preparation of compounds having the Formula X, more particularly, the stereospecific Formula X',

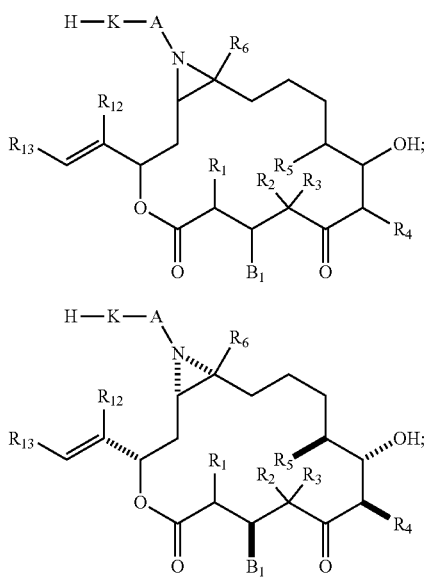

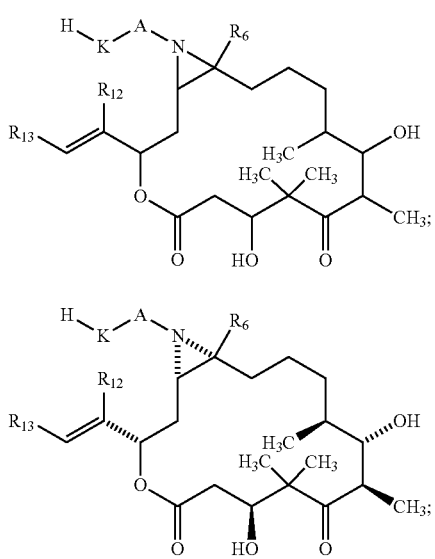

wherein K is —O—, —S—, or —NR$_7$— (more preferably O); A is C$_{2-4}$alkylene; R$_6$ is hydrogen or methyl; R$_{12}$ is H, alkyl, substituted alkyl, or halogen (more preferably methyl); and R$_{13}$ is aryl, substituted aryl, heteroaryl or substituted heteroaryl (more preferably selected from optionally-substituted thiazolyl and other preferred alternatives for R$_{13}$, above).

wherein the various radicals are selected as recited above, and K is K$_1$, A is A$_1$, or more preferably, wherein K is —O—; A is C$_{2-4}$ alkylene; B$_1$ is —OH; and the remaining groups R$_2$, R$_3$, R$_4$, R$_5$, R$_6$, R$_{12}$ and R$_{13}$ are selected from preferred alternatives for these radicals, e.g., as recited above for "in each of the alternative processes herein," including any combinations of these preferred selections.

In another embodiment, processes are provided for making compounds having the formulae Xa or Xa', The present invention processes also may also be used to prepare compounds having the formula Xb or Xb',

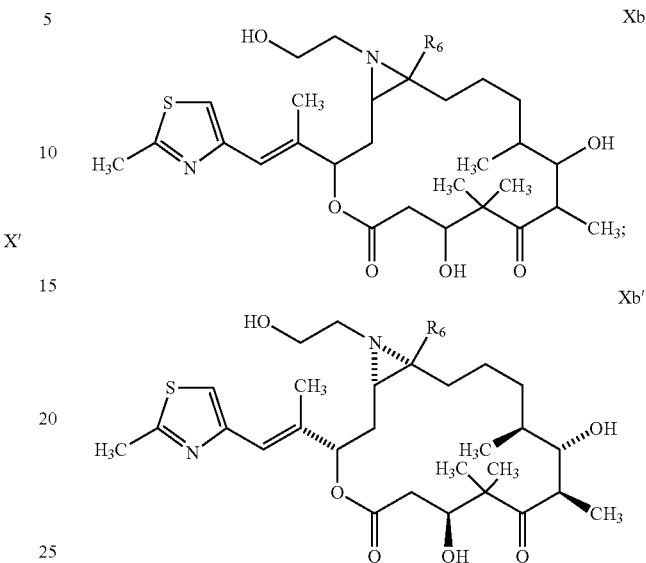

including pharmaceutically-acceptable salts and/or solvates thereof, wherein R$_6$ is hydrogen or methyl (more preferably hydrogen).

Another embodiment of the invention comprises use of any of the processes described herein to make compounds of formula X, Xa, Xa', Xb, and/or Xb', wherein the groups K, A, B$_1$R$_1$, R$_2$, R$_3$, R$_4$, R$_5$, R$_6$, R$_7$, R$_8$, R$_9$, R$_{10}$, R$_{11}$R$_{12}$, and R$_{13}$ may be selected as recited elsewhere herein, in making pharmaceutical compositions for treating cancer in patients, particularly, for use in making pharmaceutical compositions containing conjugated compounds for targeted drug delivery to tumors that over-express or preferentially express the folate receptor.

Embodiments indicated herein as exemplary or preferred are intended to be illustrative and not limiting.

Other embodiments of the invention will be apparent to one skilled in the field such as, for example, considering combinations of the embodiments referenced above, and are contemplated as covered within the scope of the invention herein.

Utility

The present invention processes may be used to prepare epothilone compounds and analogs that are useful as microtubule-stabilizing agents and as such, the compounds prepared with the present invention may be used to treat cancer and other proliferative diseases. For example, compounds having the Formula G and H, prepared according to the present invention, have microtubule stabilizing effects, as described in Regueiro-Ren et al., Organic Letters, 3:2693-2696 (2001), and U.S. patent application Ser. No. 11/753,785, titled "Azirdinyl-Epothilone Compounds," (US2007/0276018A1, published 29 Nov. 2007) filed concomitantly herewith and assigned to the present assignee, and claiming priority to U.S. provisional application Ser. No. 60/808,366, filed May 25, 2006.

The diseases that may be treated with compounds prepared according to the present invention processes may include, without limitation, the following carcinomas including those listed above and/or that of the bladder, pancreas, stomach, thyroid, and prostate;

hematopoietic tumors of lymphoid lineage, including leukemias such as acute lymphocytic leukemia and acute lymphoblastic leukemia, and lymphomas, such as B-cell lymphoma, T-cell lymphoma, Hodgkins lymphoma, non-Hodgkins lymphoma, hairy cell lymphoma, and Burkitts lymphoma;

hematopoietic tumors of myeloid lineage, including acute and chronic myelogenous leukemias and promyelocytic leukemia;

tumors of the central and peripheral nervous system, including astrocytoma, neuroblastoma, glioma, and schwannomas;

tumors of mesenchymal origin, including fibrosarcoma, rhabdomyosarcoma, and osteosarcoma; and other tumors, including melanoma, xeroderma pigmentosum, seminoma, keratoacanthoma, thyroid follicular cancer, and teratocarcinoma.

Additionally, compounds prepared according to the present invention may be used in making compounds for folate conjugates for delivery to those cancers characterized by cancer cells or tumors that express the folate receptor. The term "folate-receptor associated condition" as used herein comprises diseases or disorders characterized by expression of the folate receptor, or in other words, those diseases or disorders that can be diagnosed or treated based on the level of expression of the folate receptor in diseased tissue as compared with normal tissue. The present invention processes are useful to prepare certain compounds that are particularly useful for forming conjugates, particularly folate-conjugates.

The folate receptor is one of the proteins that is over-expressed or preferentially expressed in certain cancer cells. Folic acid is required for DNA synthesis, and certain human tumor cells are known to over-express folate-binding proteins. For example, both Campbell et al., "Folate Binding Protein is a Marker for Ovarian Cancer," *Cancer Research*, 51:5329-5338 (Oct. 1, 1991), and Coney et al., "Cloning of a Tumor-Associated Antigen: MOv18 and MOv19 Antibodies Recognize Folate-binding Protein," *Cancer Research*, 51:6125-6131 (Nov. 15, 1991), report that folate-binding proteins are markers for ovarian cancer. As a non-limiting example, such folate-receptor associated cancers include ovarian cancer and cancers of the skin, breast, lung, colon, nose, throat, mammary gland, liver, kidney, spleen, and/or brain; mesotheliomas, pituitary adenoma, cervical cancer, renal cell carcinoma or other renal cancer, choroid plexus carcinoma, and epithelial tumors (See, Asok, A., "Folate Receptors: Reflections on a Personal Odyssey and a Perspective on Unfolding Truth," *Advanced Drug Delivery Reviews*, 56:1059-1066 (2004)). Folate-receptor over-expression is known for skin, renal, breast, lung, colon, nose, throat, mammary gland, and brain cancers, as well as other cancers referenced herein.

Compounds prepared using the invention may be used to form the following conjugated compound of the formula I:

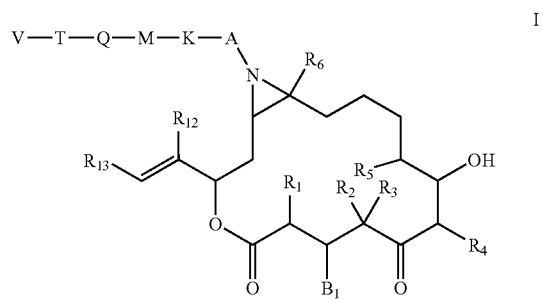

wherein:

V is folate, or an analog or derivative thereof;

Q is O, S, or $NR_7$;

M is a releasable linker;

K is O, S, or $NR_{7a}$;

A is $-(CR_8R_9)-(CH_2)_m-Z-$ wherein Z is $-(CHR_{10})-$, $-C(=O)-$, $-C(=O)-C(=O)-$, $-OC(=O)-$, $-N(R_{11})C(=O)-$, $-SO_2-$, or $-N(R_{11})SO_2-$;

$B_1$ is hydroxyl or cyano and $R_1$ is hydrogen or $B_1$ and $R_1$ are taken together to form a double bond;

$R_2$, $R_3$, and $R_5$ are, independently, hydrogen, alkyl, substituted alkyl, aryl or substituted aryl; or $R_2$ and $R_3$ may be taken together with the carbon to which they are attached to form an optionally substituted cycloalkyl;

$R_4$ is hydrogen, alkyl, alkenyl, substituted alkyl, substituted alkenyl, aryl, or substituted aryl;

$R_6$ is hydrogen, alkyl or substituted alkyl;

$R_{7a}$, $R_7$, $R_8$, $R_9$, $R_{10}$, and $R_{11}$ are independently hydrogen, alkyl, substituted alkyl, cycloalkyl, substituted cycloalkyl, aryl, substituted aryl, heterocycloalkyl, substituted heterocycloalkyl, heteroaryl, or substituted heteroaryl;

$R_{12}$ is H, alkyl, substituted alkyl, or halogen;

$R_{13}$ is aryl, substituted aryl, heteroaryl or substituted heteroaryl;

m is 0 to 6;

T has the formula:

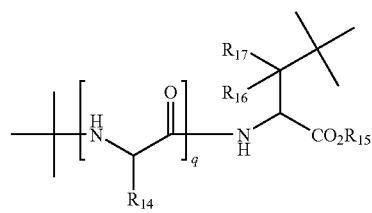

wherein $R_{14}$ at each occurrence is, independently, hydrogen, alkyl, substituted alkyl, aryl, substituted aryl, arylalkyl, substituted arylalkyl, cycloalkyl, substituted cycloalkyl, cycloalkylalkyl, substituted cycloalkylalkyl, heteroaryl, heteroarylalkyl, substituted heteroarylalkyl, substituted heteroaryl, heterocycloalkyl, or substituted heterocycloalkyl;

q is 1 to 10; and $R_{15}$, $R_{16}$ and $R_{17}$ are independently hydrogen, alkyl, substituted alkyl, or cycloalkyl.

As another nonlimiting example, the invention may be used to prepare conjugated compounds having the above formula I, wherein V is a folate-receptor binding moiety, having the formula:

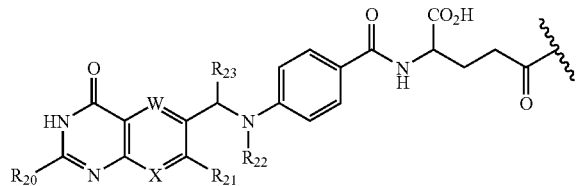

wherein W and X are independently CH or nitrogen; $R_{20}$ is hydrogen, amino or lower alkyl; $R_{21}$ is hydrogen, lower alkyl, or forms a cycloalkyl group with $R_{23}$; $R_{22}$ is hydrogen, lower alkyl, lower alkenyl, or lower alkynyl; and $R_{23}$ is hydrogen or forms a cycloalkyl with $R_{21}$; or, more preferably, where V is

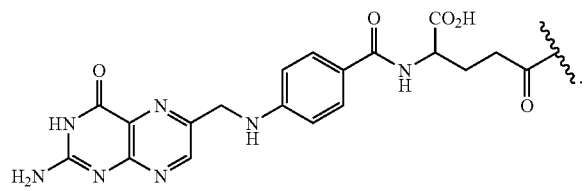

According to another embodiment, the processes of this invention can be used to prepare conjugated compounds having the following Formula Ib:

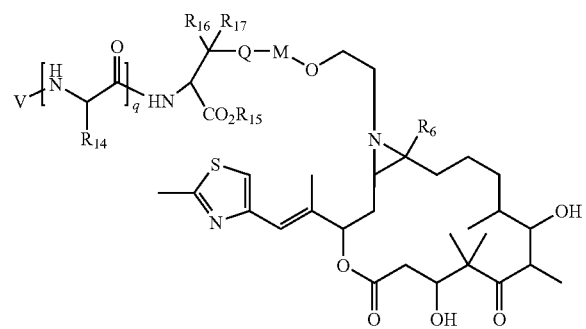

wherein V is a folate-receptor binding moiety (more preferably where V is as defined immediately above); Q is O, S, or $NR_7$; M is a releasable linker having the following formula:

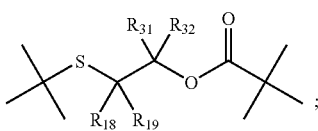

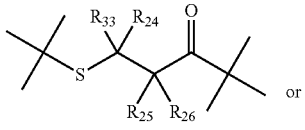

or

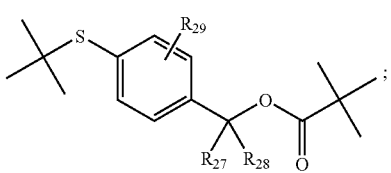

more preferably

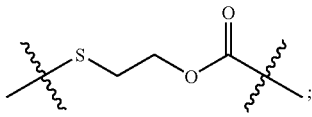

$R_{14}$ at each occurrence is, independently, hydrogen, alkyl, substituted alkyl, aryl, substituted aryl, arylalkyl, substituted arylalkyl, cycloalkyl, substituted cycloalkyl, cycloalkylalkyl, substituted cycloalkylalkyl, heteroaryl, heteroarylalkyl, substituted heteroarylalkyl, substituted heteroaryl, heterocycloalkyl, or substituted heterocycloalkyl; and is preferably a group selected from H, methyl, guanidinylpropyl, $-(CH_2)_{1-2}$ $-CO_2H$, $-CH_2-SH$, $-CH_2-OH$, imidazolyl(methyl), aminobutyl, and $-CH(OH)-CH_3$, and is more preferably a $C_1$ to $C_3$ alkyl substituted with one of $-C(=O)-OH$ or $-NH-C(=NH)-NH_2$; q is 1 to 10; preferably 1 to 5 (more preferably 1 to 3); $R_6$ is hydrogen or methyl; $R_{15}$, $R_{16}$ and $R_{17}$ are independently hydrogen, lower alkyl or substituted lower alkyl; and $R_{18}$, $R_{19}$, $R_{31}$, $R_{32}$, $R_{33}$, $R_{24}$, $R_{25}$, $R_{26}$, $R_{27}$, $R_{28}$ and $R_{29}$ are each, independently, H, lower alkyl, substituted lower alkyl, cycloalkyl, or substituted cycloalkyl, or any of $R_{18}$ and $R_{19}$; $R_{31}$ and $R_{32}$; $R_{19}$ and $R_{31}$; $R_{33}$ and $R_{24}$; $R_{25}$ and $R_{26}$; $R_{24}$ and $R_{25}$; or $R_{27}$ and $R_{28}$ may be taken together to form a cycloalkyl.

The present invention processes are especially useful for making certain aziridinyl analogs that may be used to form conjugated compounds for targeted drug delivery, e.g., conjugated compounds having the following formula:

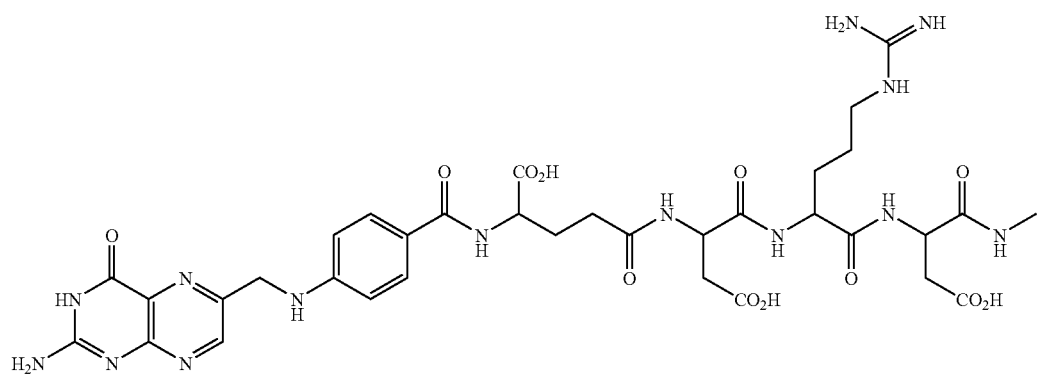

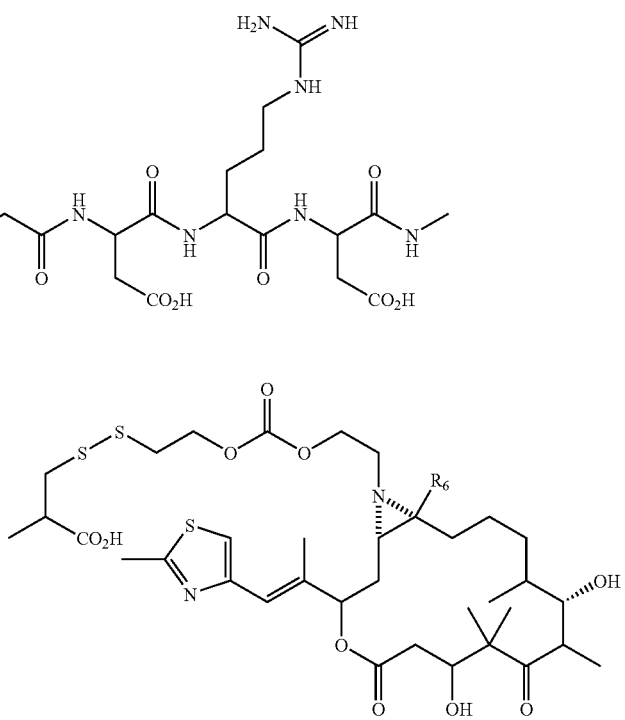

wherein $R_6$ is hydrogen or methyl. For any bivalent group listed herein that is capable of insertion into compounds of the formulae recited herein, the insertion should be made from left to right. For example, in the following situation where A is defined as —$(CR_8R_9)$—$(CH_2)_m$—Z—, the methylene group is attached to K, and the Z group is attached to the nitrogen of the aziridinyl ring, as follows:

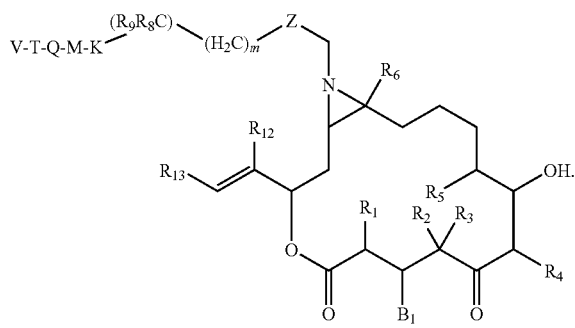

The pharmaceutical compositions prepared using the present invention processes can also be formulated or co-administered with other therapeutic agents that are selected for their particular usefulness in administering therapies associated with the aforementioned conditions. For example, the pharmaceutical compositions may be formulated with agents to prevent nausea, hypersensitivity and gastric irritation, such as antiemetics, and $H_1$ and $H_2$ antihistaminics.

One embodiment of the invention comprises use of the present invention processes in preparing pharmaceutical compositions for treatment of cancer, particularly for use in preparing pharmaceutical compositions for use in targeted drug delivery to tumors that overexpress or preferentially express the folate receptor. The pharmaceutical compositions of the present invention can be administered for any of the uses described herein by any suitable means, for example, parenterally, such as by subcutaneous, intravenous, intramuscular, or intrasternal injection or infusion techniques (e.g., as sterile injectable aqueous or non-aqueous solutions or suspensions), and/or in dosage unit formulations containing non-toxic, pharmaceutically acceptable vehicles or diluents. The pharmaceutical compositions can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution (0.9% Sodium Chloride Injection [Normal Saline] or 5% Dextrose Injection), or other suitable dispersing or wetting and suspending agents, including synthetic mono- or diglycerides, and fatty acids. Pharmaceutically acceptable compositions and/or methods of administering compounds prepared using the invention may include use of cosolvents including, but not limited to ethanol, N,N dimethylacetamide, propylene glycol, glycerol and polyethylene glycols, e.g., polyethylene glycol 300 and/or polyethylene glycol 400, may comprise use of surfactants (pharmaceutically-acceptable surface active agent that may be used to increase a compound's spreading or wetting properties by reducing its surface tension), including without limitation, CREMOPHOR®, SOLUTOL HS 15®, polysorbate 80, polysorbate 20, poloxamer, pyrrolidones such as N-alkylpyrrolidone (e.g., N-methylpyrrolidone) and/or polyvinylpyrrolidone; may also comprise use of one or more "buffers" (e.g., an ingredient which imparts an ability to resist change in the effective acidity or alkalinity of a medium upon the addition of increments of an acid or base), including, without limitation, sodium phosphate, sodium citrate, diethanolamine, triethanolamine, L-arginine, L-lysine, L-histidine, L-alanine, glycine, sodium carbonate, tromethamine (a/k/a tris[hydroxymethyl]aminomethane or Tris), and/or mixtures thereof.

The effective amount of the compound prepared with the present invention can be determined by one of ordinary skill in the art, and includes exemplary dosage amounts for an adult human of from about 0.01-10 mg/kg of body weight of active compound per day, which can be administered in a single dose or in the form of individual divided doses, such as from 1 to 4 times per day. A preferred range includes a dosage of about 0.02 to 5 mg/kg of body weight, with a range of about 0.05-0.3, being most preferred. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to microtubule-stabilization associated conditions.

Abbreviations

The following abbreviations are used in the schemes and Examples herein for ease of reference:
CBZ-OSu=N-(Benzyloxycarbonyloxy)succinimide
DCM=dichloromethane
DEA=diethylamine
DIAD=diisopropyl azodicarboxylate
DIPEA=diisopropylethylamine
DMA=dimethylamine
DMF=dimethyl formamide
DMSO=dimethylsufoxide
EDC=1-(3-dimethylaminopropyl)-3-ethylcarbodiimide hydrochloride
EtOH=ethanol
EtOAc=ethyl acetate
FR=folate receptor
HOBt=n-hydroxy benzotriazole
HPCL=high performance liquid chromatography
iPr-OH or IPA=isopropyl alcohol
LC/MS=liquid chromatography/mass spec
LDA=lithium diisopropylamide
MeOH=methanol
OTES=o-triethylsilyl
OMs=mesylate
Ph=phenyl
Pd/C=palladium on carbon
PyBOP=benzotriazol-1-yl-oxytripyaolidinophosphonium hexafluorophosphate
Py=pyridyl
RT=room temperature
Sat'd=saturated
THF=tetrahydrofuran
TFA=trifluoroacetic acid
TLC=thin layer chromatography
TESCL=chlorotriethylsilane
UV=ultraviolet The invention will now be further described with reference to the following illustrative examples.

EXAMPLES

Example 1

(i) Preparation of [4S,7R,8S,10R,9S,13R,16S]-4,8,13-trihydroxy-14-iodo-5,5,7,9-tetramethyl-16-[(E)-1-[2-methylthiazol-4-yl]prop-1-en-2-yl]oxacyclohexadecane-2,6-dione

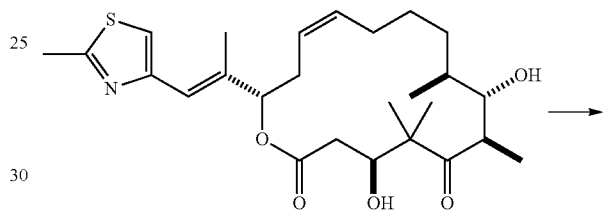

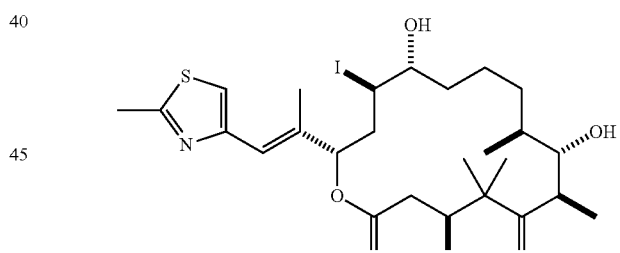

Epothilone C (54.3 g, 113.7 mmol) was dissolved in acetonitrile (480 mL) and water (50 mL). The solution was cooled to −5° C. to −10° C. Iodine (144.3 g, 568.4 mmol) was added to the reaction and the reaction was held at least for 15 hr.

The reaction was quenched with 15% sodium metabisulfite solution (900 mL). The mixture was extracted with ethyl acetate (2×1.1 L). Organic phases were collected and washed successively with saturated sodium bicarbonate solution (675 mL) and saturated sodium chloride solution (675 mL). The solvents were evaporated under reduced pressure to give crude Compound A as yellow oil (85.6 g). The Compound A was used in next reaction without further purification.

HPLC: Phenomex Luna C8 (2) 3 um, 4.6×150 mm, isocratic, 18 min, 36% B, 17 min, 56% B, (Mobile phase A=0.01M NH4OAc in ACN:Water (5:95), Mobile phase B=0.01M NH4OAc in ACN:Water (95:5)), flow rate at 1.0 ml/min, UV 245, Rt=22.4 min.

(ii) Preparation of [1R,3S,7S,10R,11S,12S,16S]-7,11-dihydroxy-8,8,10,12-tetramethyl-3-[(E)-1-[2-methylthiazol-4-yl]prop-1-en-2-yl]-4,17-dioxabicyclo[14.1.0]heptadecane-5,9-dione

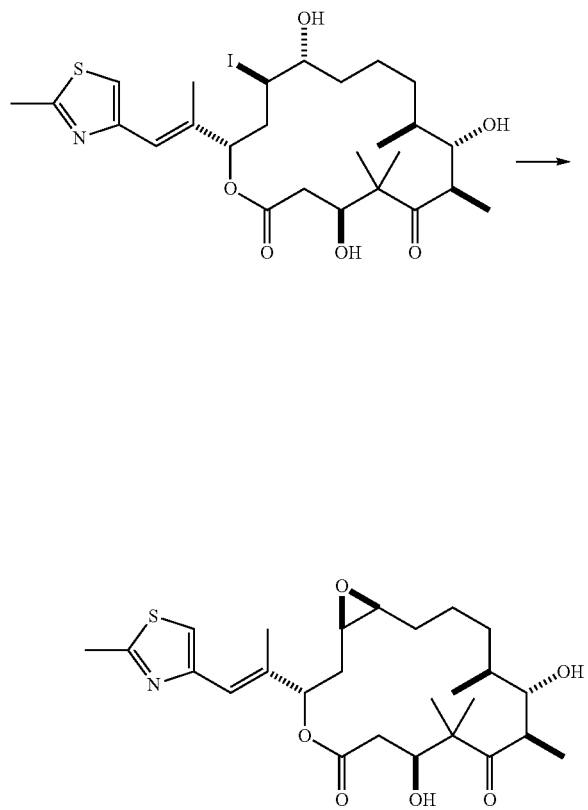

[4S,7R,8S,10R,9S,13R,16S]-4,8,13-trihydroxy-14-iodo-5,5,7,9-tetramethyl-16-[(E)-1-[2-methylthiazol-4-yl]prop-1-en-2-yl]oxacyclohexadecane-2,6-dione (85.6 g) was dissolved in acetonitrile (670 mL) and water (130 mL). Triethylamine (135 mL, 968.5 mmol) was added to the solution. The reaction was heated to 50° C. to 60° C. for at least 8 hr.

After it was cooled to RT, the solution was concentrated under reduced pressure. The residue was diluted with EtOAc (1.2 L) and washed with saturated sodium chloride solution (3×500 mL). The solvents were evaporated under reduced pressure to give the crude product as yellow oil. Purification by silica gel pad filtration (silica gel 700 g, 66% EtOAc in heptane, 2×4 L, and 1×3 L) afforded Compound B as foam (50.3 g, 90% yield) with HPLC AP 80. HPLC: Phenomex Luna C8 (2) 3 um, 4.6×150 mm, isocratic, 18 min, 36% B, 17 min, 56% B, (Mobile phase A=0.01M NH4OAc in ACN:Water (5:95), Mobile phase B=0.01M NH4OAc in ACN:Water (95:5)), flow rate at 1.0 ml/min, UV 245, Rt=15.0 min.

Example 2

(i) Preparation of (4S,7R,8S,9S,13R,14R,16S)-13-Azido-4,8,14-trihydroxy-5,5,7,9-tetramethyl-16-((E)-1-(2-methylthiazol-4-yl)prop-1-en-2-yl)oxacyclohexadecane-2,6-dione and (4S,7R,8S,9S,13S,14S,16S)-14-Azido-4,8,13-trihydroxy-5,5,7,9-tetramethyl-16-((E)-1-(2-methylthiazol-4-yl)prop-1-en-2-yl)oxacyclohexadecane-2,6-dione

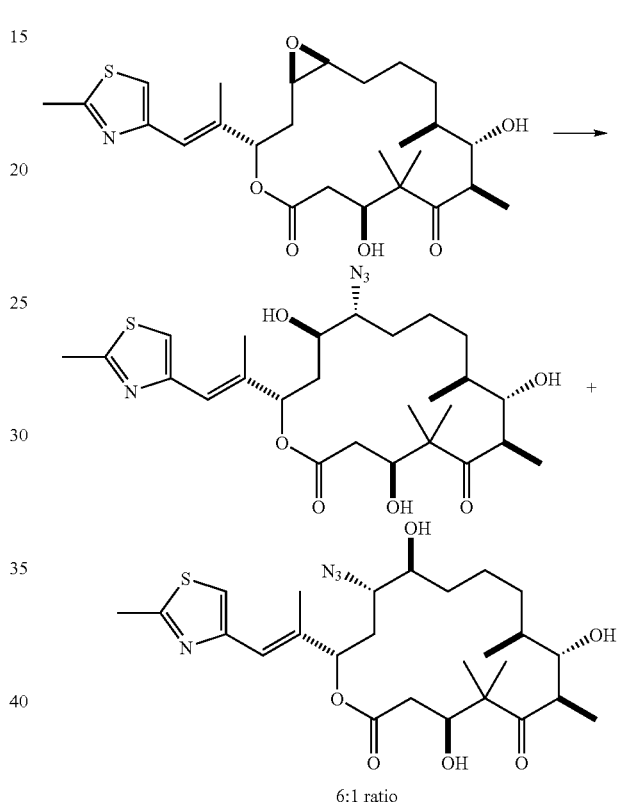

6:1 ratio

To a stirred solution of epi-Epothilone-A (14.35 g, 29.07 mmol) in ethanol (240 mL) and water (48 mL) was added sodium azide (11.45 g, 174.41 mmol) and ammonium chloride (3.14 g, 58.14 mmol). The mixture was stirred at 60° C. for 17-20 h. Volatiles were evaporated on the rotary evaporator under reduced pressure below 50° C. The residue was dissolved in ethyl acetate (287 mL) and water (50 mL) mixture. Phases were separated and the bottom aqueous phase was extracted with ethyl acetate (115 mL). The combined organic phases were washed with 25% aqueous sodium chloride (brine) solution. Solvent was evaporated under reduced pressure and the residue was passed through a pad of silica gel eluting with ethyl acetate/n-heptane (2:1) mixture. Evaporation of the solvent under reduced pressure provided regioisomeric mixture of azido-alcohols, (4S,7R,8S,9S,13R,14R,16S)-13-Azido-4,8,14-trihydroxy-5,5,7,9-tetramethyl-16-((E)-1-(2-methylthiazol-4-yl)prop-1-en-2-yl) oxacyclohexadecane-2,6-dione and (4S,7R,8S,9S,13S,14S,16S)-14-Azido-4,8,13-trihydroxy-5,5,7,9-tetramethyl-16-((E)-1-(2-methylthiazol-4-yl)prop-1-en-2-yl) oxacyclohexadecane-2,6-dione in ~6:1 ratio (12.8 g, 82%) as a white foam.

LC-MS: Phenomenex Luna C8(2) column 3 μm, 4.6×50 mm. Gradient: 15 min, 0% B to 100% B in 10 min, then 100% B for 5 min. Mobile phases: A=0.01 M NH$_4$OAc in CH$_3$CN/H$_2$O 5:95; B=0.01 M NH$_4$OAc in CH$_3$CN/H$_2$O 95:5. Flow rate: 3.0 mL/min. Wavelength: UV 250 nm. Retention time=5.52 min. MS (ESI) (M+H)$^+$=537.69.

This reaction also works in other solvents as described above, for example, using acetone, acetonitrile, tetrahydrofuran, 2-propanol, dimethylformamide, methylsulfoxide and N-methyl-pyrrolidinone.

Other azide donor agents can be used, as defined above, including tetrabutylammonium azide reagent.

(ii) Preparation of (1S,3S,7S,10R,11S,12S16R)-7,11-dihydroxy-8,8,10,12-tetramethyl-3-((E)-1-(2-methylthiazol-4-yl)prop-1-en-2-yl)-4-oxa-17-azabicyclo(14.1.0)heptadecane-5,9-dione

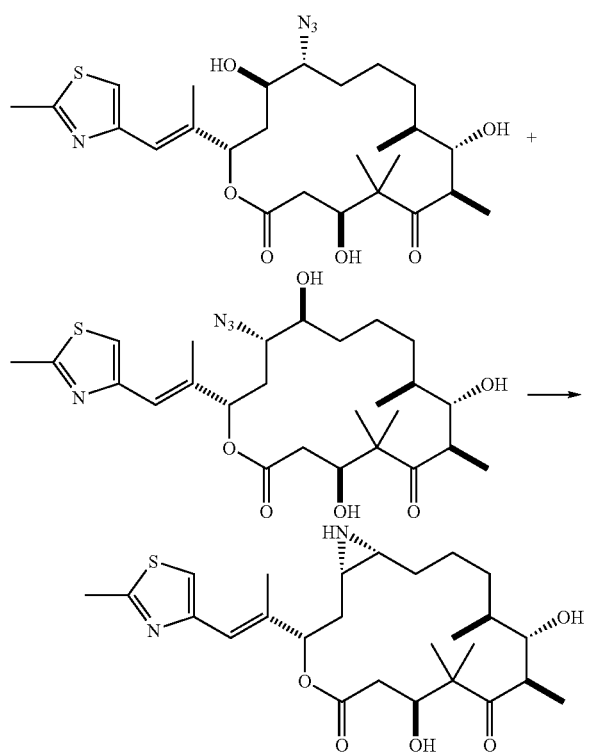

To a stirred solution of (4S,7R,8S,9S,13R,14R,16S)-13-Azido-4,8,14-trihydroxy-5,5,7,9-tetramethyl-16-((E)-1-(2-methylthiazol-4-yl)prop-1-en-2-yl)oxacyclohexadecane-2,6-dione and (4S,7R,8S,9S,13S,14S,16S)-14-Azido-4,8,13-trihydroxy-5,5,7,9-tetramethyl-16-((E)-1-(2-methylthiazol-4-yl)prop-1-en-2-yl)oxacyclohexadecane-2,6-dione mixture (12.8 g, 23.85 mmol) in anhydrous acetonitrile (90 mL) was added triphenylphosphine (9.48 g, 35.77 mmol) under nitrogen atmosphere. The clear solution was stirred at 20-40° C. for 19-40 h. The reaction mixture was cooled to 0-5° C. for 3-4 h and filtered the product. The cake was washed with heptane (64 mL) and dried at 40° C. under reduced pressure for 15-18 h to give (1S,3S,7S,10R,11S,12S16R)-7,11-dihydroxy-8,8,10,12-tetramethyl-3-((E)-1-(2-methylthiazol-4-yl)prop-1-en-2-yl)-4-oxa-17-azabicyclo(14.1.0)heptadecane-5,9-dione as a white solid (5.41 g, 46%).

LC-MS: Phenomenex Luna C8(2) column: 3 μm, 4.6×50 mm. Gradient: 15 min, 0% B to 100% B in 10 min, then 100% B for 5 min. Mobile phases: A=0.01 M NH$_4$OAc in CH$_3$CN/H$_2$O 5:95; B=0.01 M NH$_4$OAc in CH$_3$CN/H$_2$O 95:5. Flow rate: 3.0 mL/min. Wavelength: UV 250 nm. Retention time=4.43 min. MS (ESI) (M+H)$^+$=493.68.

This reaction also works with other phosphines like, tricyclohexylphosphine, trimethylphosphine, tributylphosphine and tris(4-methoxyphenyl)-phosphine and another solvent tetrahydrofuran.

Example 3

Preparation of [1S-[1R*,3R*(E),7R*,10S*,11R*,12R*,16S*]]-7,11-Dihydroxy-17-[2-hydroxyethyl]-8,8,10,12-tetramethyl-3-[1-methyl-2-(2-methyl-4-thiazolyl)ethenyl]-4-oxa-17-azabicyclo[14.1.0]heptadecane-5,9-dione

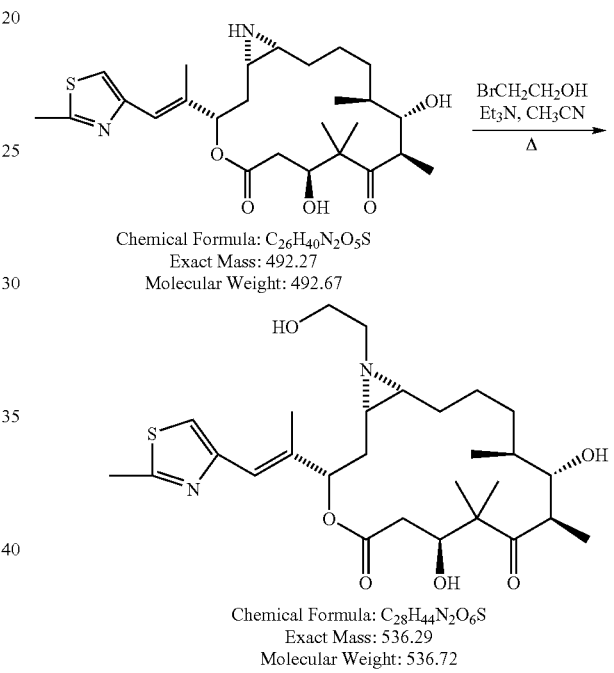

Et$_3$N (4.95 mL, 35.52 mmol) and 2-bromoethanol (3.02 mL, 42.62 mmol) were added to (1S,3S,7S,10R,11S,12S,16R)-7,11-dihydroxy-8,8,10,12-tetramethyl-3-((E)-1-(2-methylthiazol-4-yl)prop-1-en-2-yl)-4-oxa-17-azabicyclo[14.1.0]heptadecane-5,9-dione (3.50 g, 7.10 mmol) in acetonitrile (35 mL) and heated to 72.5° C. After 20 hr, the reaction mixture was cooled to room temperature, concentrated to dryness through rotary vacuum distillation. The crude was dissolved in ethyl acetate (50 mL) and mixed with deionized water (35 mL). The mixture was extracted with ethyl acetate (3×35 mL), dried over Na$_2$SO$_4$, filtered, concentrated, crystallized in acetonitrile (35 mL), washed with acetonitrile (2×5 mL), and dried in vacuum oven at 45.5° C. overnight to isolate (1S,3S,7S,10R,11S,12S,16R)-7,11-dihydroxy-17-(2-hydroxyethyl)-8,8,10,12-tetramethyl-3-((E)-1-(2-methylthiazol-4-yl)prop-1-en-2-yl)-4-oxa-17-azabicyclo[14.1.0]heptadecane-5,9-dione as a white crystalline powder (2.60 g, HPLC AP 97.1, 68.2% yield).

LC-MS: Phenomenex C8, 3 μm, 4.6×150 mm, gradient, 10 to 50% B over 10 min, and stop at 20 min. (A=5% MeCN/H$_2$O+0.01 M NH$_4$OAc; B=95% MeOH/H$_2$O+0.01 M NH₄OAc), flow rate at 1.0 mL/min, UV 254 nm. Retention time=9.43 min. MS (ESI) M+H=537.21.

Example 4

Preparation of [1S-[1R*,3R*(E),7R*,10S*,11R*, 12R*,16S*]]-7,11-Dihydroxy-17-[2-hydroxyethyl]-8,8,10,12-tetramethyl-3-[1-methyl-2-(2-methyl-4-thiazolyl)pethenyl]-4-oxa-17-azabicyclo[14.1.0] heptadecane-5,9-dione

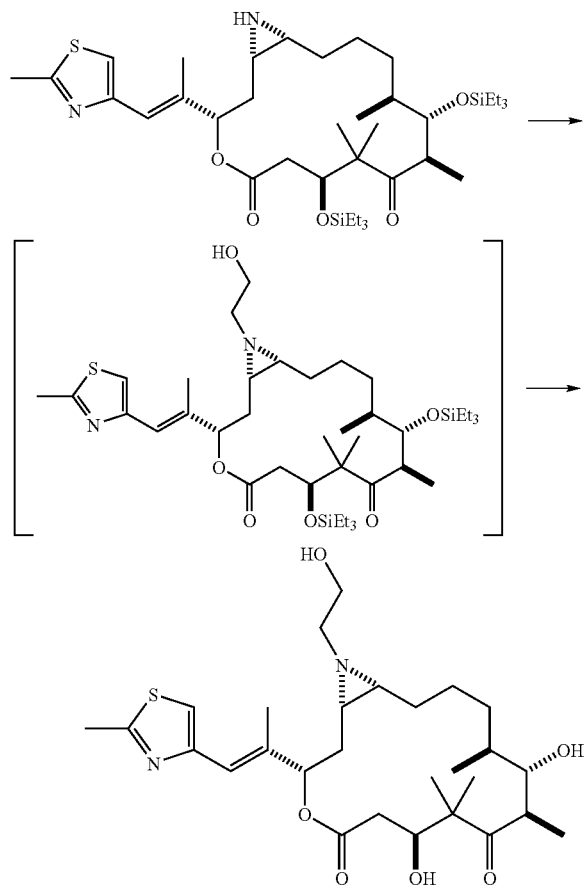

K₂CO₃ (1.4 g, 10.2 mmol) and 2-bromoethanol (0.52 mL, 7.3 mmol) were added to [1S-[1R*,3R*(E),7R*,10S*,11R*, 12R*,16S*]]-8,8,10,12-Tetramethyl-3-[1-methyl-2-(2-methyl-4-thiazolyl)ethenyl]-7,11-bis[(triethylsilyl)oxy]-4-oxa-17-azabicyclo[14.1.0]heptadecane-5,9-dione (1.05 g, 1.46 mmol) in acetonitrile (20 mL) and heated to 82° C. After 4 hr, additional 2-bromoethanol (0.52 mL, 7.3 mmol) and K₂CO₃ (1.4 g, 10.2 mmol) were added. After 5 hr, additional 2-bromoethanol (0.21 mL, 2.92 mmol) was added. After 3 hr, the reaction mixture was cooled to room temperature, filtered through Celite, washed with acetonitrile (5×5 mL), dichloromethane (2×5 mL), concentrated and taken to next step without further purification.

The crude reaction product was dissolved in dichloromethane (40 mL), cooled to 0° C., and trifluoroacetic acid (8.0 mL) was added. After 1 hr, the reaction mixture was concentrated, taken-up in saturated NaHCO₃ (200 mL), extracted with dichloromethane (3×100 mL), dried over Na₂SO₄, concentrated, and purified by silica gel chromatography (10% methanol/dichloromethane) to isolate [1S-[1R*, 3R*(E),7R*,10S*,11R*,12R*,16S*]]-7,11-Dihydroxy-17-[2-hydroxyethyl]-8,8,10,12-tetramethyl-3-[1-methyl-2-(2-methyl-4-thiazolyl)ethenyl]-4-oxa-17-azabicyclo[14.1.0] heptadecane-5,9-dione (Compound G), as a clear film (0.62 g, 79% for two steps).

LC-MS: Waters Sunfire C18, 4.6×50 mm, gradient, 0 to 100% B over 4 min. (A=10% MeOH/H₂O+0.1% TFA; B=90% MeOH/H₂O+0.1% TFA), flow rate at 4.0 mL/min, UV 220 nm. Retention time=2.12 min. MS (ESI) M+H=537.52.

Example 5

Preparation of (S)-2-(4-((2-amino-4-oxo-3,4-dihydropteridin-6-yl)methylamino)benzamido)-5-((S)-3-carboxy-1-((S)-1-((S)-3-carboxy-1-((R)-1-carboxy-2-(2-(2-((2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethoxy) carbonyloxy)ethyl)disulfanyl)ethylamino)-1-oxopropan-2-ylamino)-5-guanidino-1-oxopentan-2-ylamino)-1-oxopropan-2-ylamino)-5-oxopentanoic acid

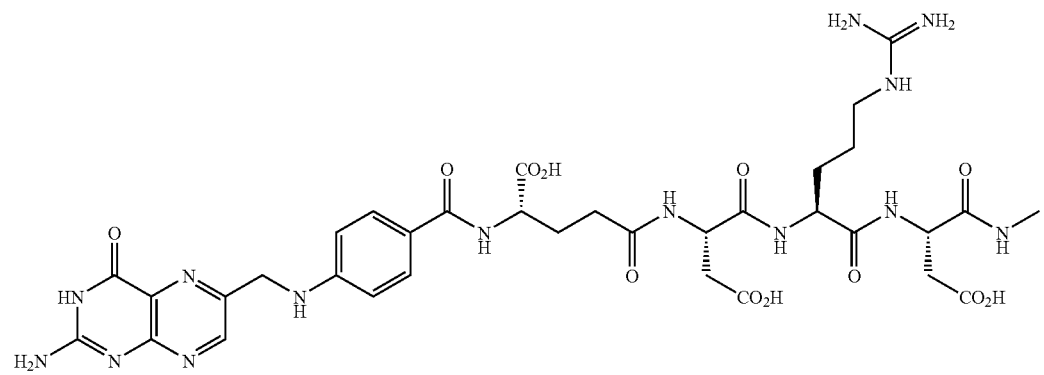

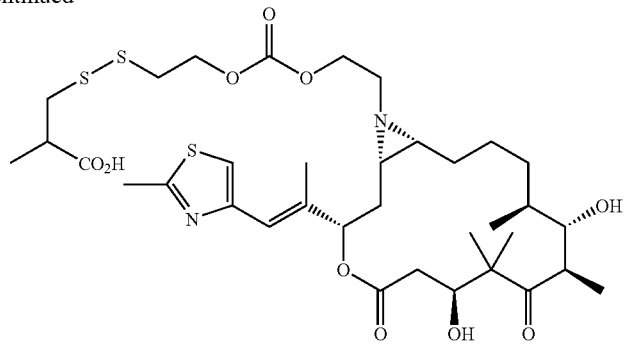

(i) Preparation of (S)-2-(4-((2-amino-4-oxo-3,4-dihydropteridin-6-yl)methylamino)benzamido)-5-((S)-3-carboxy-1-((S)-1-((S)-3-carboxy-1-((S)-1-carboxy-2-mercaptoethylamino)-1-oxopropan-2-ylamino)-5-guanidino-1-oxopentan-2-ylamino)-1-oxopropan-2-ylamino)-5-oxopentanoic acid

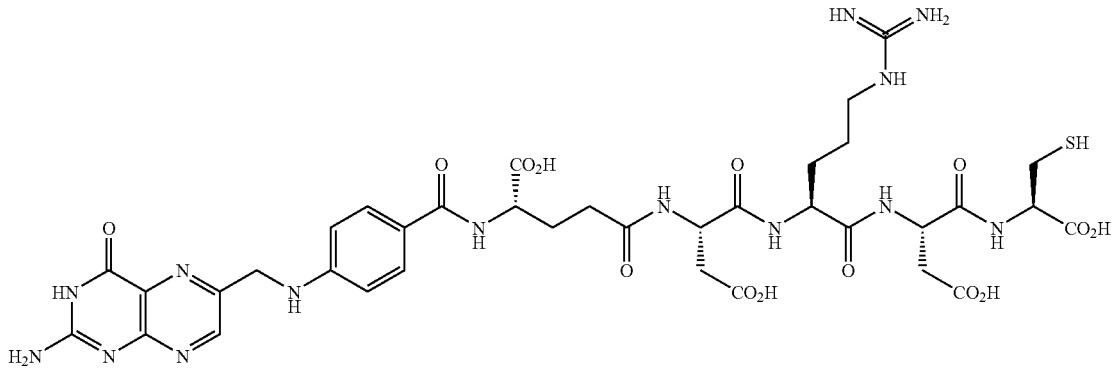

(S)-2-(4-((2-amino-4-oxo-3,4-dihydropteridin-6-yl)methylamino)benzamido)-5-((S)-3-carboxy-1-((S)-1-((S)-3-carboxy-1-((S)-1-carboxy-2-mercaptoethylamino)-1-oxopropan-2-ylamino)-5-guanidino-1-oxopentan-2-ylamino)-1-oxopropan-2-ylamino)-5-oxopentanoic acid was synthesized by solid phase peptide synthesis in five steps starting from H-Cys(4-methoxytrityl)-2-chlorotrityl-resin. The Table 1 shows the amount of reagents used in the synthesis.

TABLE 1

| | Mmol | Equiv. | MW | Amount |
|---|---|---|---|---|
| H-Cys(4-methoxytrityl)-2-chlorotrityl-Resin (loading 0.57 mmol/g) | 1.14 | | | 2.0 g |
| Fmoc-Asp(OtBu)-OH (dissolve in 15 mL DMF) | 1.14 | 2 | 411.5 | 0.938 g |
| Fmoc-Arg(Pbf)-OH (15 mL DMF) | 1.14 | 2 | 648 | 1.477 g |
| Fmoc-Asp(OtBu)-OH (dissolve in 15 mL DMF) | 1.14 | 2 | 411.5 | 0.938 g |
| Fmoc-Glu-OtBu (15 mL DMF) | 1.14 | 2 | 425.5 | 0.970 g |
| $N^{10}$TFA Pteroic Acid (dissolve in 15 mL DMSO) | 1.14 | 1.25 | 408 | 0.581 g |

TABLE 1-continued

| | Mmol | Equiv. | MW | Amount |
|---|---|---|---|---|
| DIPEA | 1.14 | 4 | 174 | 0.793 |
| PyBOP | 1.14 | 2 | 520 | 1.185 g |

The following procedures were used:

Coupling Steps:

To the resin in a peptide synthesis vessel were added the amino acid solution, DIPEA, and PyBOP. The mixture was bubbled for 1 hr and washed 3× with DMF and isopropyl alcohol. FMOC deprotection was effected by treatment with 20% piperidine in DMF, 2× (10 min), before each amino acid coupling. This sequence was repeated for each amino acid coupling step.

Synthesis of $N^{10}$-TFA-Protected Pteroic Acid:

To 10 L of 0.1 M tris base solution (121.1 g tris base in 10 L water) in a 22 L mechanically-stirred round bottomed flask, equipped with a heating mantle, was added 200 g (0.453 mole) of folic acid. The mixture was stirred to dissolve the folic acid, and then 500 mg (3.67 mmole) zinc chloride was added. Carboxypeptidase G (13×20 unit vials available from Sigma) was added and the pH was adjusted to 7.3 with 1N HCl and maintained throughout the reaction. The mixture was protected from light and heated at 30° C. for 8-10 days (use of an auto-titrator to hold the pH constant reduced the conversion time by 4-5 days). The reaction was monitored by analytical HPLC until 80% conversion was achieved (further conversion is desirable but has not been optimized). The product was precipitated from the reaction mixture by adjusting the solution to pH=3.0 using 6N HCl. The slurry was transferred to a centrifuge vial and centrifuged at 4000 rpm for 10 min. The supernatant was decanted. The wet solid was then directly purified as follows (the wet solid could be frozen for storage or first freeze-dried; however, storage of wet solids in the freezer until dissolution was more efficient). To 40 g of crude pteroic acid in 700 mL of water was added 1.0 M NaOH until pH=11.5. The mixture was filtered (Whatman type 1) and then chromatographed (column: 10×120 cm; stationary phase: 8 kg DEAE cellulose; mobile phase: 1.0 M NaCl/0.01 M NaOH, pH=11.5; flow rate: 17 ml/min). One liter yellow-colored fractions were collected and analyzed by HPLC. Fractions containing pure pteroic acid were adjusted to pH=3 with 6 M HCl to precipitate pteroic acid. The mixture was centrifuged at 3000 rpm for 20 min. The supernatant was decanted and washed with water (3×). The solid was freeze-dried for at least 72 hr. The impact of residual water on the next reaction is not known.

The pteroic acid was further dried over $P_2O_5$ under high vacuum for over 24 hr (note that similar results in the protection step were obtained without this additional drying step). Next, 100 g (0.32 mol) of pteroic acid was added to a 5 L round bottom flask, equipped with a mechanical stirrer and an argon inlet, and stored under high vacuum overnight. Argon gas was added followed by 3500 g (2316 mL) of trifluoroacetic anhydride. The flask was sealed with a rubber stopper or argon inlet adaptor, and then stirred vigorously. The flask was protected from light and stirred at room temperature under argon atmosphere for 7 days (the reaction was monitored by HPLC of aliquots diluted 20× each with water and DMSO). The mixture was rotary evaporated to dryness and treated with 2.5 L of 3% trifluoroacetic acid in water. The mixture was stirred overnight at room temperature to hydrolyze anhydride by-products. Rotary evaporation gave a dry solid. The solid was suspended in 2 L of water and then centrifuged in 250-mL centrifuge bottles at 3000 rpm for 20 min. The supernatant was removed and the solid was washed with water and centrifuged (4 times). The solid was freeze-dried for 3 days, transferred to amber bottles, and dried under high vacuum in the presence of $P_2O_5$ for 2 days (Purity≧95%; residual TFA assessed by Elemental Analysis).

Cleavage Step:

The protected intermediate was released from the resin using the cleavage reagent prepared from 92.5% (50 mL) TFA, 2.5% (1.34 mL) $H_2O$, 2.5% (1.34 mL) Triisopropylsilane, and 2.5% (1.34 mL) ethanedithiol. The cleavage reagent was added to the reaction vessel (25 mL). Argon was bubbled through the mixture for 1.5 hr. The liquid was drained from the vessel, and resin was washed with remaining reagent (3×8 mL). The volatiles were concentrated by rotary evaporation to a volume of 10 mL. Diethyl ether (35.0 mL) was added to effect precipitation. The solid was collected by centrifugation and dried to give 1.25 g of cleavage product.

Deprotection Step:

The $N^{10}$-trifluoroacetyl protecting group in the pteroic acid portion was removed under basic conditions. Starting with 250 mg of protected intermediate in 10 mL water, the pH was adjusted to 9.3 and maintained for 1 hr using 4:1$H_2O$:ammonium hydroxide (1-2 mL). After 1 hr, the pH was adjusted to 5 with 1N HCl (~1 mL) and the product was purified on preparative HPLC to yield 125 mg of Compound H.

HPLC Purification Conditions:

Column: Waters NovaPak $C_{18}$ 300×19 mm

Solvent A: Buffer 10 mM Ammonium Acetate, pH=5

Solvent B: Acetonitrile

Elution: 1% B to 20% B in 40 min at 15 mL/min

Total yield from combined reactions: 625 mg (ii) Preparation of 2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethyl 2-(2-(pyridin-2-yl)disulfanyl)ethyl carbonate

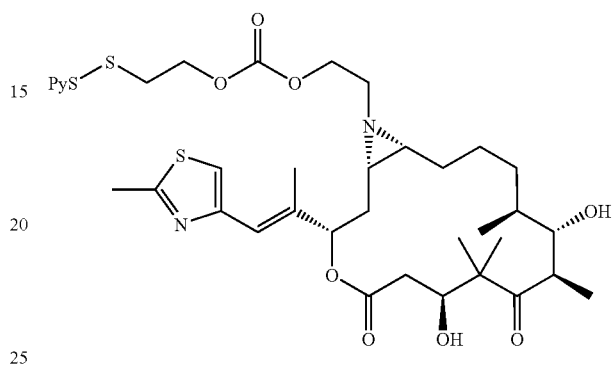

A. Preparation of 2-(2-(Pyridin-2-yl)disulfanyl)ethanol

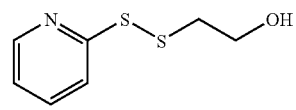

To a solution of methoxycarbonyl sulfenyl chloride (10 mL, 110 mmol), in dichloromethane (100 mL), cooled to 0° C., was added mercaptoethanol (7.6 mL, 110 mmol), dropwise. The reaction mixture was allowed to stir at 0° C. for 30 min. At this point, a solution of 2-mercaptopyridine (12.2 g, 110 mmol) in dichloromethane (160 mL) was added. The solution was allowed to react at 0° C. for 1 hr and then was allowed to warm to RT for another 1 hr. Solid product was observed to have fallen out of solution. TLC (1:1 Pet Ether/EtOAc) showed that significant product had been formed. The reaction mixture was concentrated to a volume of 125 mL. The mixture was filtered through a Buchner funnel The filter cake was washed with dichloromethane and then dried under vacuum overnight to afford 2-(2-(Pyridin-2-yl)disulfanyl)ethanol (23.6 g), as the HCl salt.

TLC: $R_f$=0.45

Plates—EMD Silica Gel 60 $F_{254}$, 5×10 cm, 250 M

B. Preparation of Benzo[d][1,2,3]triazol-1-yl2-(2-(pyridin-2-yl)disulfanyl)ethyl carbonate (Compound I)

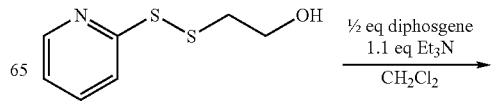

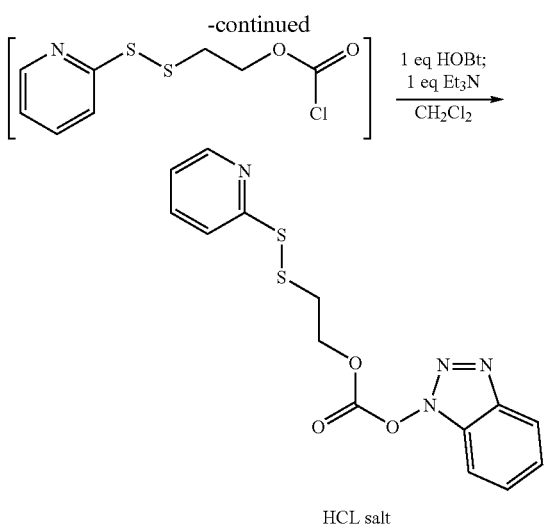

A solution of diphosgene (2.28 g, 11.5 mmol) in 15 mL anhydrous dichloromethane was stirred under argon in a roundbottom flask and cooled by a ice/salt bath. An addition funnel with a mixture of 2-(pyridin-2-yldisulfanyl)ethanol (5.01 g, 22.4 mmol) and triethylamine (2.25 g, 22.2 mmol) in 65 mL anhydrous dichloromethane was placed onto the roundbottom flask. The mixture was added dropwise over a period of 20 min. The reaction mixture was allowed to warm to RT and stirred for an additional 1 hr. TLC analysis of the reaction mixture showed that the starting material was consumed and there was formation of a "streaking" less polar chloroformate product, TLC (6:4 EtOAc:Hexanes): $R_F$ of starting material 0.4; $R_F$ of chloroformate product: 0.8.

The reaction mixture was stirred in a roundbottom flask under argon and cooled by an ice/salt bath. A mixture of 3.02 g, 22.4 mmol HOBt and 2.23 g, 22.0 mmol triethylamine in 10 mL anhydrous dichloromethane was added to a dropping funnel affixed to the roundbottom flask. The mixture was slowly added to the roundbottom flask maintaining the reaction temperature at 2° C. The reaction mixture was allowed to warm to RT and stirred overnight. Approximately 27 mL of dichloromethane was then distilled from the reaction mixture at atmospheric pressure. The mixture was then allowed to cool to RT and stir for 2 hr. The solids were collected by filtration, and the filter cake was washed with 20 mL of dichloromethane. The solids were then dried under vacuum at 40° C. on a rotary evaporator to afford 7.81 g of off-white solids. This product was analyzed by $^1$H-NMR and determined to be the desired product.

C. Preparation of 2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethyl 2-(2-(pyridin-2-yl)disulfanyl)ethyl carbonate

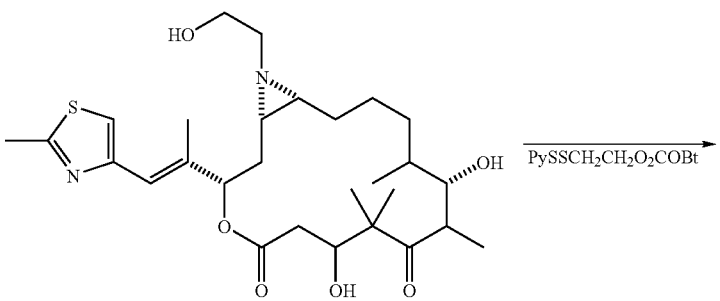

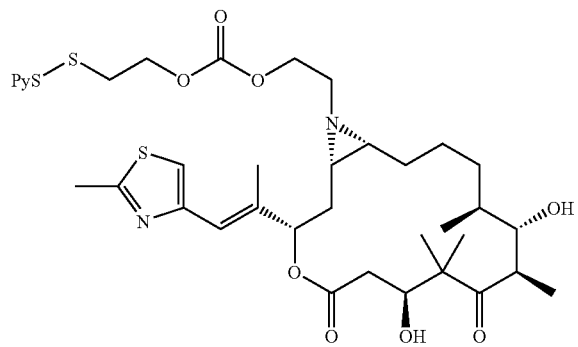

To a solution of [1S-[1R*,3R*(E),7R*,10S*,11R*,12R*, 16S*]]-7,11-Dihydroxy-17-[2-hydroxyethyl]-8,8,10,12-tetramethyl-3-[1-methyl-2-(2-methyl-4-thiazolyl)ethenyl]-4-oxa-17-azabicyclo[14.1.0]heptadecane-5,9-dione in anhydrous dichloromethane at 0° C. was added DMAP (1.2 eq.) and benzo[d][1,2,3]triazol-1-yl2-(2-(pyridin-2-yl)disulfanyl)ethyl carbonate (1.0 eq.) in tandem. The reaction mixture was stirred at 0° C. under argon and monitored by TLC every 10 min. Additional DMAP (1.2 eq.) and Compound I (2)(1.0 eq.) were added as necessary until all of Compound G was consumed. The reaction was quenched with MeOH (1 mL) at 0° C., the solvent was removed under vacuum, and the residue was purified by chromatography (silica gel, 2.5-5% MeOH in DCM) to afford the title compound as a beige solid. Compound amounts and recoveries are listed below in Table 2. Total yield from 2.95 g of Compound G was 2.80 g (67.9%) of Compound I.

TABLE 2

| | Compound G (mg) | Compound I (2) (mg) | DMAP (mg) | DCM (mL) | Compound I (mg)* |
|---|---|---|---|---|---|
| Batch #1 | 303 | 197 × 3 | 82.8 × 3 | 8.0 | 204 |
| Batch #2 | 952 | 683 × 3 | 260 × 3 | 22.0 | 984 |
| Batch #3 | 921 | 661 × 3 | 251 × 3 | 22.0 | 761 |
| Batch #4 | 775 | 556 × 3 | 211 × 3 | 18.0 | 851 |

*Each chromatographic purification typically gave pure product along with some impure (80-90% purity) product. The impure product was combined with the crude product from the next batch for chromatographic purification. For batches #2 and 4, two chromatographic purifications were carried out.

(iii) Preparation of (S)-2-(4-((2-amino-4-oxo-3,4-dihydropteridin-6-yl)methylamino)benzamido)-5-((S)-3-carboxy-1-((S)-1-((S)-3-carboxy-1-((R)-1-carboxy-2-(2-(2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethoxy)carbonyloxy)ethyl)disulfanyl)ethylamino)-1-oxopropan-2-ylamino)-5-guanidino-1-oxopentan-2-ylamino)-1-oxopropan-2-ylamino)-5-oxopentanoic acid

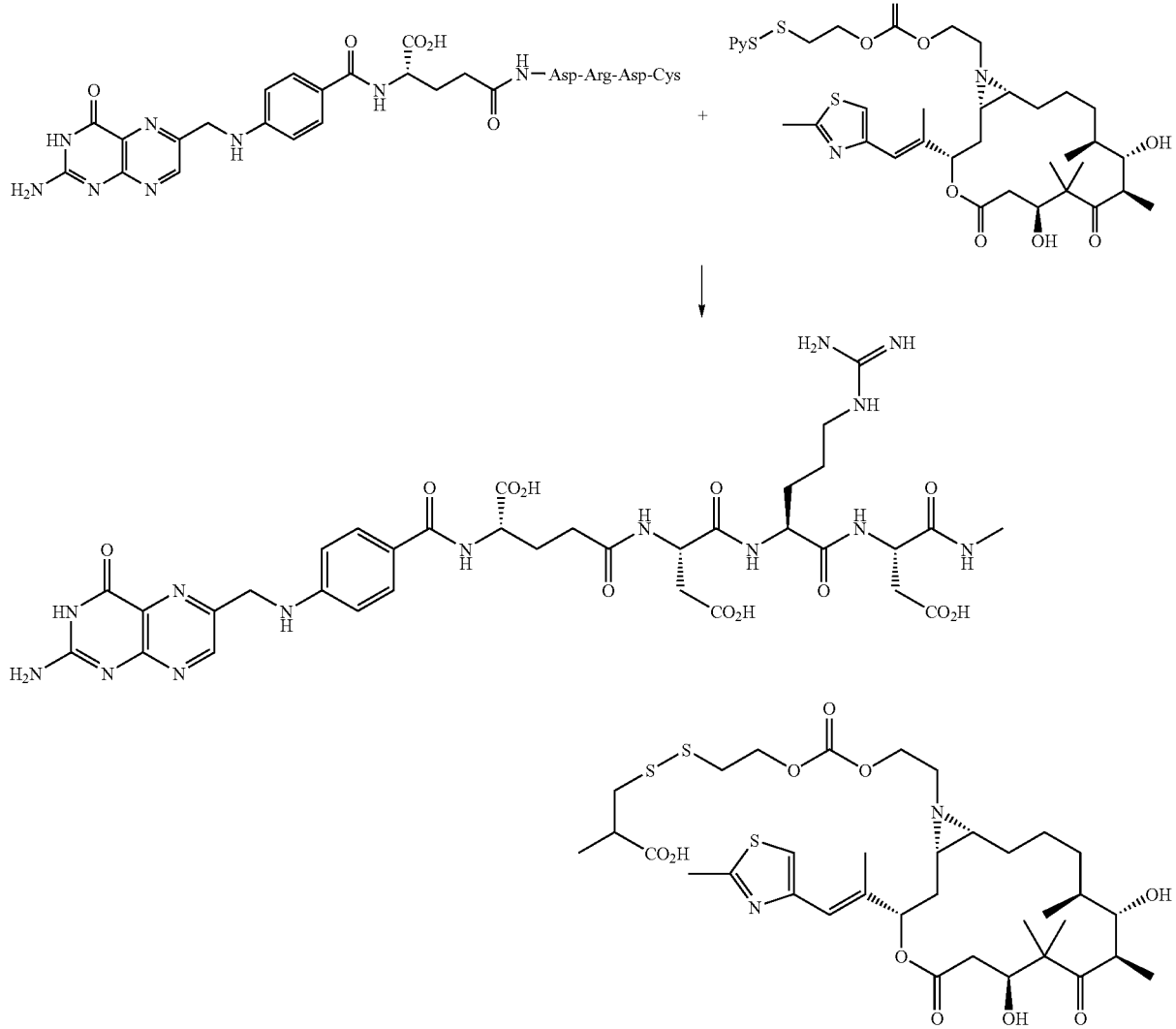

To 15 mL of H$_2$O (bubbled with argon for 10 min before use) was added to (S)-2-(4-((2-amino-4-oxo-3,4-dihydropteridin-6-yl)methylamino)benzamido)-5-((S)-3-carboxy-1-((S)-1-((S)-3-carboxy-1-((S)-1-carboxy-2-mercaptoethylamino)-1-oxopropan-2-ylamino)-5-guanidino-1-oxopentan-2-ylamino)-1-oxopropan-2-ylamino)-5-oxopentanoic acid (498 mg, 0.534 mmol) in a 50 mL size centrifuge tube. To this suspension, while bubbling with argon, was added dropwise saturated NaHCO$_3$ solution (bubbled with argon for 10 min before use) until the pH of the resulting solution reached 6.9. 2-((1S,3S,7S,10R,11S,12S,16R)-7,11-dihydroxy-8,8,10,12-tetramethyl-3-((E)-1-(2-methylthiazol-4-yl)prop-1-en-2-yl)-5,9-dioxo-4-oxa-17-aza-bicyclo[14.1.0]heptadecan-17-yl)ethyl 2-(2-(pyridin-2-yl)disulfanyl)ethyl carbonate (400 mg, 0.534 mmol) in THF was added quickly and the resulting homogenous solution was stirred under argon for 30 min. The reaction progress was checked by analytical HPLC at 15 min. The product peak came out at ~6.4 min under analytical HPLC conditions. The mixture was diluted with ~15 mL of phosphate buffer and the THF was removed under vacuum. The cloudy solution was centrifuged and filtered. The yellow filtrate was divided into two portions and purified by preparative HPLC. Pure fractions (>98% pure) were pooled and freeze-dried. Tail fractions (<98% pure) were collected and re-purified for every 3-6 chromatography runs to provide 700 mg of the title compound as a white powder (contains 11.8% by weight of water and 8.7% by weight sodium and sodium phosphate salts, as determined by Karl Fischer and elemental analyses).

Preparative HPLC Parameters:
    Column: Waters Nova-Pak HR C18 6 µm 30×300 mm
    Mobile phase A: 7.0 mM sodium phosphate buffer, pH=7.2
    Mobile phase B: acetonitrile
    Method: 10% B-50% B in 30 min, flow rate: 40 mL/min Analytical HPLC Parameters:
    Column: Waters Symmetry C18 3.5 µm 4.6×75 mm
    Mobile phase A: 10 mM Triethylammonium acetate (TEAOAc) buffer, pH=7.5
    Mobile phase B: Acetonitrile
    Method: 20% B-40% B in 10 min, flow rate: 1.0 mL/min
    Accurate mass m/z (C$_{67}$H$_{92}$N$_{16}$O$_{22}$S$_3$):
    Calculated: 1570.58907 (M+2H), 785.29454 (M+2H)$^{2+}$, 523.86563 (M+3H)$^{3+}$, 393.15118 (M+4H)$^{4+}$.
    Found: (M+2H)$^{2+}$ at 785.29100 (4.5 ppm), (M+3H)$^{3+}$ at 523.86431 (2.5 ppm), (M+4H)$^{4+}$ at 393.14996 (3.1 ppm).

The invention claimed is:

1. A process for making a compound having the formula A.1,

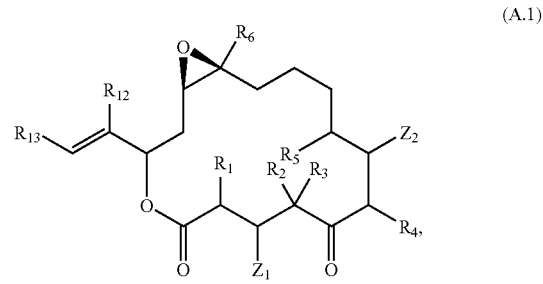

(A.1)

wherein $R_1$ is hydrogen or forms a bond with $Z_1$;

$Z_1$ is hydroxyl, cyano, is taken together with $R_1$ to form a bond, or is $OR_p$;

$Z_2$ is hydroxyl or $OR_p$; wherein each $R_p$ is a protecting group;

$R_2$, $R_3$, and $R_5$ are independently, hydrogen, alkyl, substituted alkyl, aryl or substituted aryl; or $R_2$ and $R_3$ may be taken together with the carbon to which they are attached to form an optionally-substituted cycloalkyl;

$R_4$ is hydrogen, alkyl, substituted alkyl, alkenyl, alkynyl, aryl, or substituted aryl;

$R_6$ is hydrogen, alkyl or substituted alkyl;

$R_{12}$ is H, alkyl, substituted alkyl, or halogen; and $R_{13}$ is aryl, substituted aryl, heteroaryl or substituted heteroaryl;

which comprises,
    reacting a compound having the formula (C),

---

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Conjugant Linker

<400> SEQUENCE: 1

Asp Arg Asp Cys

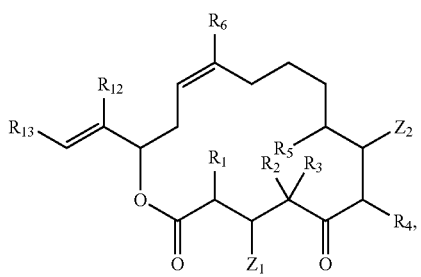

(C)

wherein $R_1$, $R_2$, $R_3$, $R_4$, $R_5$, $R_6$, $R_{12}$, $R_{13}$, $Z_1$ and $Z_2$ are as described above, with at least one halogenating agent to provide compounds having the formula (B.1) and/or (B.2), wherein Y is halogen and $R_1$, $R_2$, $R_3$, $R_4$, $R_5$, $R_6$, $R_{12}$, $R_{13}$, $Z_1$ and $Z_2$ are as described above

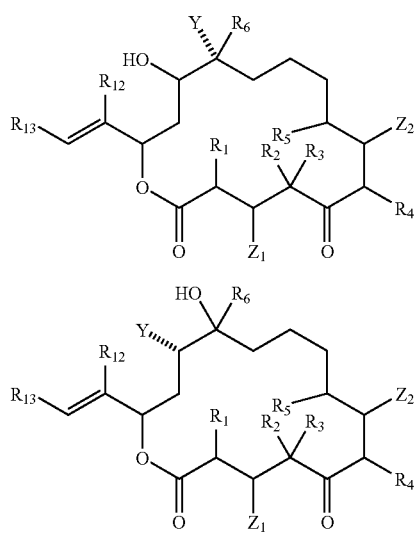

(B.1)

+

(B.2)

followed by treatment of compounds (B.1) and/or (B.2) with base to provide the compound of formula A.1.

2. The process of claim 1, wherein the step of halogenating the compounds of formula C is performed in a polar solvent and at reduced temperature.

3. The process of claim 2 wherein the reduced temperature is in the range of about 0° C. to −15° C.

4. The process of claim 1, wherein the step of treatment with base to perform epoxide ring closure is performed without isolating compounds of formula (B.1) and/or (B.2.).

5. The process of claim 1, wherein the treatment with base is performed in a polar solvent or polar/aqueous solvent system and at elevated temperature.

6. The process of claim 5 wherein the elevated temperature is between about 40° C. and the boiling point of the solvent or solvent system.

7. The process of claim 1, wherein the starting material is epothilone C or D having the formula,

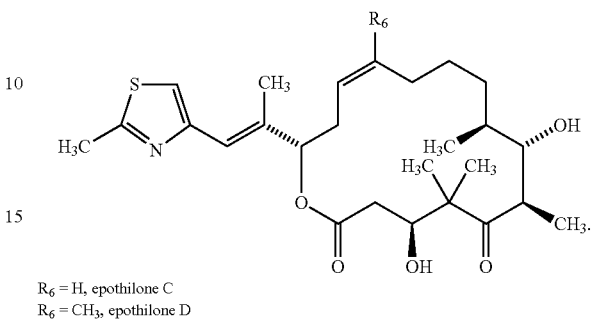

$R_6$ = H, epothilone C
$R_6$ = $CH_3$, epothilone D

8. A process according to claim 7, wherein the compound of formula A.1 is epi-epothilone A or epi-epothilone B, having the formula,

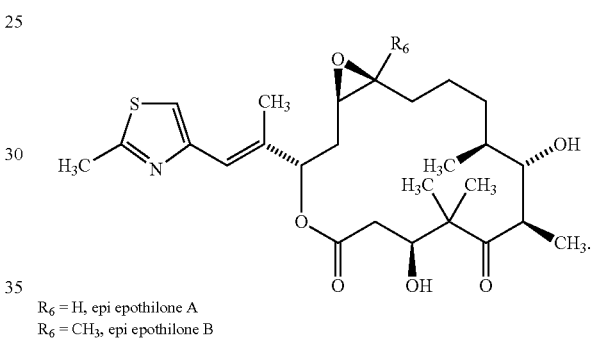

$R_6$ = H, epi epothilone A
$R_6$ = $CH_3$, epi epothilone B

9. A process according to claim 1, wherein the halogenating agent is halogen or N-halosuccinimide.

10. A process according to claim 1, wherein the halogenating agent is iodine.

11. A process according to claim 1, wherein the base is N-methylmorpholine, triethylamine, or diisopropylethylamine.

12. The process of claim 2, wherein the polar solvent is selected from the group consisting of acetonitrile, water, ethanol, and mixtures thereof.

13. The process of claim 2, wherein the polar solvent is acetonitrile.

14. The process of claim 5, wherein the polar solvent or polar/aqueous solvent system is selected from the group consisting of acetonitrile, water, ethanol, and mixtures thereof.

15. The process of claim 5, wherein the polar solvent or polar/aqueous solvent system is acetonitrile-water.

* * * * *